US011584958B2

(12) United States Patent
Jamshidi et al.

(10) Patent No.: US 11,584,958 B2
(45) Date of Patent: Feb. 21, 2023

(54) LIBRARY PREPARATION AND USE THEREOF FOR SEQUENCING BASED ERROR CORRECTION AND/OR VARIANT IDENTIFICATION

(71) Applicant: GRAIL, LLC, Menlo Park, CA (US)

(72) Inventors: Arash Jamshidi, Redwood City, CA (US); Gordon Cann, Redwood City, CA (US); Hamed Amini, Menlo Park, CA (US); Alex Aravanis, San Mateo, CA (US)

(73) Assignee: GRAIL, LLC, Menlo Park, CA (US)

( * ) Notice: Subject to any disclaimer, the term of this patent is extended or adjusted under 35 U.S.C. 154(b) by 241 days.

(21) Appl. No.: 15/942,237

(22) Filed: Mar. 30, 2018

(65) Prior Publication Data

US 2018/0291438 A1 Oct. 11, 2018

Related U.S. Application Data

(60) Provisional application No. 62/480,210, filed on Mar. 31, 2017.

(51) Int. Cl.
*C12Q 1/6855* (2018.01)
*G16B 30/00* (2019.01)
*G16B 40/00* (2019.01)
*C12Q 1/6806* (2018.01)
*C12Q 1/6869* (2018.01)
*G16B 30/10* (2019.01)
*C12N 15/10* (2006.01)

(52) U.S. Cl.
CPC ........ *C12Q 1/6855* (2013.01); *C12N 15/1065* (2013.01); *C12Q 1/6806* (2013.01); *C12Q 1/6869* (2013.01); *G16B 30/00* (2019.02); *G16B 30/10* (2019.02); *G16B 40/00* (2019.02)

(58) Field of Classification Search
CPC .................................................. C12Q 1/6855
See application file for complete search history.

(56) References Cited

U.S. PATENT DOCUMENTS

| | | | |
|---|---|---|---|
| 4,683,195 A | 7/1987 | Mullis et al. |
| 5,308,751 A | 5/1994 | Ohkawa et al. |
| 6,013,445 A | 1/2000 | Albrecht et al. |
| 6,143,496 A | 11/2000 | Brown et al. |
| 6,404,907 B1 | 6/2002 | Gilchrist et al. |
| 6,818,395 B1 | 11/2004 | Quake et al. |
| 6,833,246 B2 | 12/2004 | Balasubramanian |
| 7,169,560 B2 | 1/2007 | Lapidus et al. |
| 7,264,929 B2 | 9/2007 | Rothberg et al. |
| 7,282,337 B1 | 10/2007 | Harris et al. |
| 7,537,897 B2 | 5/2009 | Brenner et al. |
| 7,666,593 B2 | 2/2010 | Lapidus |
| 7,700,286 B2 | 4/2010 | Stroun et al. |
| 7,754,429 B2 | 7/2010 | Rigatti et al. |
| 8,168,385 B2 | 5/2012 | Brenner et al. |
| 8,318,434 B2 | 11/2012 | Cuppens |
| 8,383,345 B2 | 2/2013 | Shendure et al. |
| 8,586,310 B2 | 11/2013 | Mitra et al. |
| 8,741,606 B2 | 6/2014 | Casbon et al. |
| 8,865,410 B2 | 10/2014 | Shendure et al. |
| 9,085,798 B2 | 7/2015 | Chee |
| 9,404,156 B2 | 8/2016 | Hicks et al. |
| 9,476,095 B2 | 10/2016 | Vogelstein et al. |
| 9,752,188 B2 | 9/2017 | Schmitt et al. |
| 10,011,871 B2 | 7/2018 | Bielas |
| 10,385,393 B2 | 8/2019 | Salk et al. |
| 10,450,606 B2 | 10/2019 | Bielas |
| 2002/0164629 A1 | 11/2002 | Quake et al. |
| 2005/0019776 A1 | 1/2005 | Callow et al. |
| 2008/0261204 A1 | 10/2008 | Lexow |
| 2009/0026082 A1 | 1/2009 | Rothberg et al. |
| 2009/0099041 A1 | 4/2009 | Church et al. |
| 2009/0127589 A1 | 5/2009 | Rothberg et al. |
| 2009/0156412 A1 | 6/2009 | Harris et al. |
| 2009/0191565 A1 | 7/2009 | Lapidus et al. |
| 2009/0215633 A1 | 8/2009 | Eijk et al. |
| 2010/0035252 A1 | 2/2010 | Rothberg et al. |
| 2010/0041048 A1 | 2/2010 | Diehl et al. |
| 2010/0069263 A1 | 3/2010 | Shendure et al. |
| 2010/0137143 A1 | 6/2010 | Rothberg et al. |
| 2010/0188073 A1 | 7/2010 | Rothberg et al. |
| 2010/0197507 A1 | 8/2010 | Rothberg et al. |
| 2010/0227329 A1 | 9/2010 | Cuppens |
| 2010/0282617 A1 | 11/2010 | Rothberg et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |

(Continued)

FOREIGN PATENT DOCUMENTS

| | | |
|---|---|---|
| DE | 102008025656 | 12/2009 |
| DE | 102008025656 A1 | 12/2009 |

(Continued)

OTHER PUBLICATIONS

Illumina, Illumina Data Sheet: Sequencing, Illumina, Jan. 6, 2010. (Year: 2010).*
Thompson et al., Single Molecule Sequencing with a HeliScope Genetic Analysis System, Supplement 92, Current Protocols in Molecular Biology, 2010, 7.0.1-7.10.14. (Year: 2010).*
Rhodes et al., PacBio Sequencing and Its Applications, Genomics Proteomics Bioinformatics, 2015, 13, 278-289. (Year: 2015).*
Salk et al., Enhancing the Accuracy of Next-Generation Sequencing For Detecting Rare and Subclonal Mutations, Nature Reviews Genetics, 2018, 19, 260-285. (Year: 2018).*
Casbon et al., "A method for counting PCR template molecules with application to next-generation sequencing," (2011) Nucleic Acids Res. 39(12):e81.
Mardis et al., "The impact of next-generation sequencing technology on genetics," (2008) Trends Genet 24(2):133-141.

(Continued)

*Primary Examiner* — Amy M Bunker
(74) *Attorney, Agent, or Firm* — Haynes and Boone, LLP

(57) ABSTRACT

Aspects of the invention include methods for preparing sequencing libraries, performing sequencing procedures that can correct for process-related errors, and identifying rare variants that are or may be indicative of cancer.

9 Claims, 4 Drawing Sheets

(56) References Cited

U.S. PATENT DOCUMENTS

| | | |
|---|---|---|
| 2010/0304982 A1 | 12/2010 | Hinz et al. |
| 2012/0058468 A1* | 3/2012 | Mckeown ............... C07H 21/04 |
| | | 435/6.1 |
| 2012/0283110 A1 | 11/2012 | Shendure et al. |
| 2013/0005585 A1 | 1/2013 | Anderson |
| 2014/0155274 A1 | 6/2014 | Xie et al. |
| 2015/0044687 A1 | 2/2015 | Schmitt et al. |
| 2015/0087535 A1 | 3/2015 | Patel |
| 2015/0197798 A1 | 7/2015 | Xu et al. |
| 2015/0368708 A1 | 12/2015 | Talasaz |
| 2015/0376608 A1 | 12/2015 | Kaper et al. |
| 2016/0040229 A1 | 2/2016 | Kaper et al. |
| 2016/0046986 A1 | 2/2016 | Eltoukhy et al. |
| 2016/0251704 A1 | 9/2016 | Talasaz et al. |
| 2016/0304948 A1 | 10/2016 | Lee et al. |
| 2016/0319345 A1* | 11/2016 | Gnerre ................. C12Q 1/6869 |
| 2016/0326578 A1 | 11/2016 | Bielas |
| 2017/0136433 A1* | 5/2017 | Sun ..................... C12Q 1/6806 |
| 2018/0044731 A1 | 2/2018 | Valouev et al. |
| 2018/0363048 A1 | 12/2018 | Bielas |
| 2018/0363049 A1 | 12/2018 | Bielas |
| 2020/0048706 A1 | 2/2020 | Bielas |
| 2020/0048707 A1 | 2/2020 | Bielas |
| 2020/0299766 A1 | 9/2020 | Bielas |
| 2020/0299767 A1 | 9/2020 | Bielas |
| 2020/0385804 A1 | 12/2020 | Bielas |
| 2021/0054455 A1 | 2/2021 | Bielas |
| 2021/0222243 A1 | 7/2021 | Bielas |
| 2021/0238676 A1 | 8/2021 | Bielas |
| 2021/0238678 A1 | 8/2021 | Bielas |
| 2021/0246504 A1 | 8/2021 | Bielas |
| 2021/0317525 A1 | 10/2021 | Bielas |
| 2021/0317526 A1 | 10/2021 | Bielas |
| 2021/0340619 A1 | 11/2021 | Bielas |
| 2021/0388435 A1 | 12/2021 | Bielas |
| 2021/0395818 A1 | 12/2021 | Bielas |

FOREIGN PATENT DOCUMENTS

| | | |
|---|---|---|
| DE | 10 2008 025656 | 7/2016 |
| EP | 2828218 | 1/2015 |
| EP | 2814959 B1 | 1/2018 |
| JP | 4747245 | 8/2011 |
| WO | 1993/006239 | 4/1993 |
| WO | 96/12039 | 4/1996 |
| WO | 98/44151 | 10/1998 |
| WO | 00/18957 | 4/2000 |
| WO | 00/60124 | 10/2000 |
| WO | 2004/003136 | 1/2004 |
| WO | 2004/065582 A2 | 8/2004 |
| WO | 2004/081183 | 9/2004 |
| WO | 2005/042759 | 5/2005 |
| WO | 2005/063980 | 7/2005 |
| WO | 2005/068656 | 7/2005 |
| WO | 2006/084130 | 8/2006 |
| WO | 2006/137733 | 12/2006 |
| WO | 2007/037678 | 4/2007 |
| WO | 2007/073165 | 6/2007 |
| WO | 2007/073171 | 6/2007 |
| WO | 2007/106509 | 9/2007 |
| WO | 2007/114693 | 10/2007 |
| WO | 2008/093098 A2 | 8/2008 |
| WO | 2009/036525 | 3/2009 |
| WO | 2009/152928 | 12/2009 |
| WO | 2010/115100 | 10/2010 |
| WO | 2010/115154 | 10/2010 |
| WO | 2010/126614 | 11/2010 |
| WO | 2010/127186 A1 | 11/2010 |
| WO | 2011/155833 | 12/2011 |
| WO | 2012/038839 | 3/2012 |
| WO | 2012/106546 | 8/2012 |
| WO | 2012/142213 | 10/2012 |
| WO | 2012/148477 | 11/2012 |
| WO | 2013/123442 | 8/2013 |
| WO | 2013/138510 A1 | 9/2013 |
| WO | 2013/142389 | 9/2013 |
| WO | 2013/181170 | 12/2013 |
| WO | 2015/094861 | 6/2015 |
| WO | 2015/200609 | 12/2015 |
| WO | 2016/176091 | 11/2016 |
| WO | 2017/040306 | 3/2017 |
| WO | 2017/100441 | 6/2017 |
| WO | 2017/218512 | 12/2017 |
| WO | 2018/031760 | 2/2018 |
| WO | 2018/031929 | 2/2018 |

OTHER PUBLICATIONS

Extended European Search Report from EP Application No. 18150361.6, dated Jun. 13, 2018.

Bainbridge et al., "Whole exome capture in solution with 3 Gbp of data," (2010) Genome Biology 11:R62.

Baird et al., "Rapid SNP Discovery and Genetic Mapping Using Sequenced RAD markers," (2008) PLOS One 3(10):e3376, 1-7.

Bettegowda et al., "Detection of circulating tumor DNA in early- and late-stage human malignancies," (2014) SciTrans Med 6(224):1-11.

Bielas et al., "Human cancers express a mutator phenotype," (2006) Proc. Natl. Acad. Sci. USA 103(48):18238-18242.

Bielas et al., "Quantification of random genomic mutations," (2005) Nature Methods 2(4):285-290.

Bowtell, "The genesis and evolution of high-grade serous ovarian cancer" (2010) Nat. Rev. Cancer 10(11):803-808.

Brandon et al., "Mitochondrial mutations in cancer," (2006) Oncogene 25(34):4647-4662.

Braslavsky et al., "Sequence information can be obtained from single DNA molecules," K2003) PNAS 100(7):3960-3964.

Brockman et al., "Quality scores and SNP detection in sequencing-by-synthesis systems," (2008) Methods 18:763-770.

Cancer Genome Atlas Research Net, "Integrated Genomic Analyses of Ovarian Carcinoma," (2011) Nature 474(7353):609-615.

Chatterjee et al., "Mitochondrial DNA mutations in human cancer," (2006) Oncogene 25(34):4663-4674.

Chmielecki et al., "Targeted next-generation sequencing of DNA regions proximal to a conserved GXGXXG signaling motif enables systematic discovery of tyrosine kinase fusions in cancer," (2010) Nucleic Acids Research 38(20):6985-6996.

Copeland et al., "Mitochondrial DNA Alterations in Cancer," (2002) Cancer Invest. 20(4):557-569.

Duncavage et al., "Hybrid Capture and Next-Generation Sequencing Identify Viral Integration Sites from Formalin-Fixed, Paraffin-Embedded Tissue," (2011) J Mol Diagn., 13(3):325-333.

Fleishmann et al., "Whole-genome random sequencing and assembly of Haemophilus influenzae Rd," (1995) Science 269(5223):496-512.

Fullwood et al., "Next-generation DNA sequencing of paired-end tags (PET) for transcriptome and genome analyses," (2009) Genome Res 19:521-532.

Harris et al., "Single-Molecule DNA Sequencing of a Viral Genome," (2008) Science 320:106-109.

Hashimoto et al., "5'-end SAGE for the analysis of transcriptional start sites," (2004) Nature Biotechnology 22:1146-1149.

Hiatt et al., "Parallel, tag-directed assembly of locally derived short sequence reads," (2010) Nature Methods 7(2):119-122.

Homer et al., "Improved variant discovery through local re-alignment of short-read next-generation sequencing data using SRMA," (2010) Genome Biology, 11:R99.

Hug et al., "Measurement of the No. of Molecules of a Single mRNA Species in a Complex mRNA Preparation," (2003) J. Theor. Biol. 221(4):615-624.

Huse et al., "Accuracy and quality of massively parallel DNA pyrosequencing," (2007) Genome Biology 8:RI43.

Jabara et al., "Accurate sampling and deep sequencing of the HIV-1 protease gene using a Primer ID," (2011) Proc Natl Acad Sci USA 108(50):20166-20171.

(56) References Cited

OTHER PUBLICATIONS

Jones et al., "Comparative lesion sequencing provides insights into tumor evolution," (2008) Proc Natl Acad Sci USA 105(11):4283-4288.
Kinde et al., "Detection and quantification of rare mutations with massively parallel sequencing," (2011) Proc Natl Acad Sci USA 108(23):9530-9535.
Kivioja et al., "Counting absolute numbers of molecules using unique molecular identifiers," (2011) Nat Methods 9(1):72-4.
Korbel et al., "Paired-End Mapping Reveals Extensive Structural Variation in the Human Genome," (2007) Science 318(5849) 420-426.
Kou et al., "Benefits and Challenges with Applying Unique Molecular Identifiers in Next Generation Sequencing to Detect Low Frequency Mutations," (2016) PLoS One 11(1):e0146638.
Kraytsberg et al., "Single molecule PCR in mtDNA mutational analysis: genuine mutations vs. damage bypass-derived artifacts," (2008) Methods 46(4):269-273.
Li et al., "A new approach for detecting low-level mutations in next-generation sequence data," (2012) Genome Biology 13:R34.
Linnarsson, "Recent advances in DNA sequencing methods—general principles of sample preparation," (2010) Experimental Cell Research 316:1339-1343.
Marguiles et al., "Genome sequencing in microfabricated high-density picolitre reactors," (2005) Nature 437(7057):376-380.
Maxam et al., "A new method for sequencing DNA," (1977) PNAS 74(2):560-564.
McCloskey et al., "Encoding PCR products with batch-stamps and barcodes," (2007) Biochem Genet. 45(11-12):761-767.
Metzker, "Sequencing technologies—the next generation," (2010) Nature Reviews Genetics 11:31-46.
Moudrianakis et al., "Base Sequence Determination In Nucleic Acids With The Electron Microscope III. Chemistry and microscopy of guanine-labeled DNA," (1965) PNAS 53(3):564-671.
Mouliere et al., "Circulating tumor-derived DNA is shorter than somatic DNA in plasma," (2015) PNAS 112(11):3178-3179.
Mouliere et al., "Multi-marker Analysis of Circulating Cell-free DNA Toward Personalized Medicine for Colorectal Cancer," (2014) Mol Oncol 8(5):927-947.
Newman et al., "An ultrasensitive method for quantitating circulating tumor DNA with broad patient coverage," (2014) Nat Med 20(5):548-554.
Ng et al., "Gene identification signature (GIS) analysis for transcriptome characterization and genome annotation," (2005) Nature Methods 2(2):105-111.
Ng et al., "Multiplex sequencing of paired-end ditags (MS-PET): a strategy for the ultra-high-throughput analysis of transcriptomes and genomes," (2006) NAR 34(12):e84.
Niedringhaus et al., "Landscape of Next-Generation Sequencing Technologies," (2011) Anal. Chem. 83(12):4327-4341.
Saha et al., "Using the transcriptome to annotate the genome," (2002) Nature Biotechnology 20:508-512.
Sanger et al., "DNA sequencing with chain-terminating inhibitors," (1977) PNAS 74(12):5463-5467.
Schmitt et al., "Detection of ultra-rare mutations by next-generation sequencing," (2012) PNAS 109(36):14508-14513.
Shiroguchi et al., "Digital RNA Sequencing Minimizes Sequence-dependent Bias and Amplification Noise with Optimized Single-molecule Barcodes," (2012) PNAS 109(4):1347-1352.
Soni et al., "Progress toward ultrafast DNA sequencing using solid-state nanopores," (2007) Clin Chem 53(11):1996-2001.
Srivatsan et al., "High-Precision, Whole-Genome Sequencing of Laboratory Strains Facilitates Genetic Studies," (2008) PLoS Genet 4(8):e1000139.
Taylor et al., "Mitochondrial DNA mutations in human disease," (2005) Nat Rev Genet 6(5):389-402.
Travers et al., "A flexible and efficient template format for circular consensus sequencing and SNP detection," (2010) NAR 38(15):1-8.
Varley et al., "Bisulfite Patch PCR enables multiplexed sequencing of promoter methylation across cancer samples," (2010) Genome Research 20:1279-87.
Velculescu et al., "Serial analysis of gene expression," (1995) Science 270(5235):484-487.
Walsh et al., "Detection of inherited mutations for breast and ovarian cancer using genomic capture and massively parallel sequencing," (2010) PNAS 107(28):12629-12633.
Wei et al., "5' Long serial analysis of gene expression (LongSAGE) and 3' LongSAGE for transcriptome characterization and genome annotation," (2004) PNAS 101 (32):11701-11706.
Zhang et al., "The impact of next-generation sequencing on genomics," (2011) J Genet Genomics 38(3):95-109.
Zheng et al., "Origins of human mitochondrial point mutations as DNA poly m erase y-mediated errors," (2006) Mutat Res 599(1-2):11-20.
Zilberman et al., "Genome-wide analysis of DNA methylation patterns," (2007) Development doi:10.1242/dev.001131 134:3959-3965.
"European Examination Report," EP Application No. 18150361.6, dated Apr. 12, 2019, 4 pages.
"European Summons to Attend Oral Proceedings Pursuant to Rule 115(1) EPC, and Provisional Opinion," EP Patent Application No. 13706397.0, Aug. 6, 2019, 10 pages.
"European Third Party Observations," EP Application No. 18150361.6, dated Mar. 18, 2019, 22 pages.
"Notice of Opposition," EP Patent 2,814,959 and Arguments in Support of Same, Oct. 2018, 21 pages.
Beck et al., "Next Generation Sequencing of Serum Circulating Nucleic Acids from Patients with Invasive Ductal Breast Cancer Reveals Differences to Health and Nonmalilgnant Controls," (2010) Molecular Cancer Research 8(3):335-342.
Meldrum et al., "Next-Generation Sequencing for Cancer Diagnostics: a Practical Perspective," (2011) Clinical Biochemist Review 32(4):177-195.
Myllykangas et al., "Targeted sequencing library preparation by genomic DNA circularization," (2011) BMC Biotechnology 11:122.
European Search Report issued in EP Application No. 20215829.1 dated Jun. 28, 2021.
Assignment recorded with the USPTO on Apr. 8, 2013 in PCT Application No. PCT/US2013/026505, as cited in EP Opposition of EP 3363901.
Cover Sheet for U.S. Appl. No. 61/600,535, filed Feb. 17, 2012, as cited in EP Opposition of EP 3363901.
PCT Request form filed with on Feb. 15, 2013 for PCT Application No. PCT/US2013/026505, as cited in EP Opposition of EP 3363901.
UMass Chan Medical School, Lab Guidance Note, "Indexing and Barcoding for Illumina NextGen Sequencing," dated Oct. 2011, obtainable from the following web address https://www.umassmed.edu/contentassets/5ea3699998c442bb8c9b1a3cf95dbb24/indexingand-barcoding-for-illumina-nextgen-sequencing.pdf, as cited in EP Opposition of EP 3363901.
U.S. Appl. No. 61/476,150 (certified priority document), as cited in EP Opposition of EP 3363901.
U.S. Appl. No. 61/484,482 (certified priority document), as cited in EP Opposition of EP 3363901.
U.S. Appl. No. 61/600,535 (certified priority document), as cited in EP Opposition of EP 3363901.
U.S. Appl. No. 61/609,985 (certified priority document), as cited in EP Opposition of EP 3363901.
U.S. Appl. No. 61/613,413 (certified priority document), as cited in EP Opposition of EP 3363901.
U.S. Appl. No. 61/625,319 (certified priority document), as cited in EP Opposition of EP 3363901.
U.S. Appl. No. 61/625,623 (certified priority document), as cited in EP Opposition of EP 3363901.
Bentley et al., "Accurate whole human genome sequencing using reversible terminator chemistry," (2008) Nature 456(6):53-59, as cited in EP Opposition of EP 3363901.
Kaur et al., "Novel amplification of DNA in a hairpin structure: towards a radical elimination of PCR errors from amplified DNA," (2003) Nucleic Acids Research 31 (6), 7 pages, as cited in EP Opposition of EP 3363901.

(56) References Cited

OTHER PUBLICATIONS

Kinde et al., Supporting Information for "Detecting and Quantification of Rare Mutations with Massively Parallel Sequencing," (2011) PNAS 108(23):9530-9535, as cited in EP Opposition of EP 3363901.

Kircher et al., "Double indexing overcomes inaccuracies in multiplex sequencing on the Illumina platform," (2012) Nucleic Acids Research 40(1):e3, 8 pages, as cited in EP Opposition of EP 3363901.

Milbury et al., "PCR-Based Methods for the Enrichment of Minority Alleles and Mutations," (2009) Clinical Chemistry 55(4):632-640, as cited in EP Opposition of EP 3363901.

Son et al., "Preparing DNA Libraries for Multiplexed Paired-End Deep Sequencing for Illumina GA Sequencers," (2011) Curr Protoc Microbiol, CHAPTER: Unit1E.4. doi: 10.1002/9780471729259.mc01e04s2, as cited in EP Opposition of EP 3363901.

* cited by examiner

LIBRARY PREPARATION AND USE THEREOF FOR SEQUENCING BASED ERROR CORRECTION AND/OR VARIANT IDENTIFICATION

CROSS REFERENCE TO RELATED APPLICATIONS

Under 35 U.S.C. § 119(e), this application claims priority benefit of the filing date of U.S. Provisional Patent Application Ser. No. 62/480,210, filed on Mar. 31, 2017, the disclosure of which application is herein incorporated by reference in its entirety.

FIELD OF THE INVENTION

The present invention relates to molecular biology techniques and methods for preparing sequencing libraries, performing sequencing procedures that can correct for process-related errors, and identifying rare variants that are indicative of cancer.

BACKGROUND OF THE INVENTION

Analysis of circulating cell-free DNA (cfDNA) using next generation sequencing (NGS) is recognized as a valuable tool for detection and diagnosis of cancer. Identifying rare variants indicative of cancer using NGS requires deep sequencing of circulating cfDNA from a patient's test sample. However, deep sequencing has limitations. In particular, errors introduced during sample preparation and sequencing can make accurate identification of variants difficult. There is a need in the art for methods of preparing sequencing libraries, sequencing techniques that can correct for process-related errors, and techniques for identifying rare variants.

SUMMARY OF THE INVENTION

Aspects of the invention include methods for preparing sequencing libraries, performing sequencing procedures that can correct for process-related errors, and identifying rare variants that are or may be indicative of cancer. In some embodiments, a method for preparing a sequencing library involves: (a) obtaining a test sample comprising a plurality of double-stranded DNA (dsDNA) fragments, wherein the dsDNA fragments comprise a forward strand and a reverse complement strand; (b) providing a set of loop-shaped double-stranded DNA (dsDNA) adapters, the set comprising a plurality of first loop-shaped adapters and a plurality of second loop-shaped adapters, wherein each of the first and second loop-shaped adapters comprises a unique molecular identifier (UMI), and wherein the first loop-shaped adapter further comprises an endonuclease restriction site; (c) modifying the plurality of dsDNA fragments for adapter ligation; (d) ligating the plurality of first and second loop-shaped adapters to the plurality of dsDNA fragments to generate a plurality of circular adapter-dsDNA-adapter constructs; (e) cleaving the plurality of first loop-shaped adapters with an endonuclease to produce a plurality of linear single-strand DNA (ssDNA) molecules, wherein said linear ssDNA molecules comprise the forward strand and reverse complement strand; and (f) amplifying the linear ssDNA molecules to generate a sequencing library.

In some embodiments, a method for correcting sequencing derived errors in sequence reads involves: (a) obtaining a test sample comprising a plurality of double-stranded (dsDNA) fragments; (b) preparing a sequencing library, wherein preparing the sequencing library comprises: (i) providing a set of loop-shaped double-stranded DNA (dsDNA) adapters, the set comprising a plurality of first loop-shaped adapters and a plurality of second loop-shaped adapters, wherein each of the first and second loop-shaped adapters comprises a unique molecular identifier (UMI), and wherein the first loop-shaped adapter further comprises an endonuclease restriction site; (ii) ligating the plurality of first and second loop-shaped adapters to the plurality of dsDNA fragments to generate a plurality of circular adapter-dsDNA-adapter constructs; and (iii) cleaving the plurality of first loop-shaped adapters with an endonuclease to produce a plurality of linear single-strand DNA (ssDNA) molecules, wherein said linear ssDNA molecules comprise a forward strand and a reverse complement strand; (c) sequencing at least a portion of the sequencing library to obtain a plurality of sequence reads; (d) grouping the plurality of sequence reads into a plurality of families based on the UMIs, wherein each of the families comprises a first set of forward strands, each having a first UMI, and a second set of reverse complement strands, each having a second UMI, wherein the second UMI is complementary to the first UMI; and (e) comparing the sequence reads within each family to generate a consensus sequence for each of the families.

In some embodiments, a method for detecting one or more rare variants in a test sample involves: (a) obtaining a test sample comprising a plurality of double-stranded (dsDNA) fragments; (b) preparing a sequencing library, wherein preparing the sequencing library comprises: (i) providing at set of loop-shaped dsDNA adapters, the set comprising a plurality of first loop-shaped adapters and a plurality of second loop-shaped adapters, wherein each of the first and second loop-shaped adapters comprises a unique molecular identifier (UMI), and wherein the first loop-shaped adapter further comprises an endonuclease restriction site; (ii) ligating the plurality of first and second loop-shaped adapters to the plurality of dsDNA fragments to generate a plurality of circular adapter-dsDNA-adapter constructs; and (iii) cleaving the plurality of first loop-shaped adapters with an endonuclease to produce a plurality of linear single-stranded DNA (ssDNA) molecules, wherein said linear ssDNA molecules comprise the forward strand and reverse complement strand; (c) sequencing at least a portion of the sequencing library to obtain a plurality of sequence reads; (d) grouping the plurality sequence reads into a plurality of families based on the UMIs, wherein each of the families comprises a first set of forward strands, each having a first UMI, and a second set of reverse complement strands, each having a second UMI, wherein the second UMI is complementary to the first UMI; (e) comparing the sequence reads within each family to generate one or more consensus sequences for each of the families; (f) aligning the one or more consensus sequences to a reference sequence; and (g) identifying a consensus sequence as a rare variant if the consensus sequence differs from the reference sequence at one or more nucleotide positions.

In some embodiments, the dsDNA fragments are cell-free DNA (cfDNA) fragments. In some embodiments, the cfDNA fragments originate from healthy cells and from cancer cells. In some embodiments, the test sample comprises whole blood, a blood fraction, plasma, serum, urine, feces, saliva, a tissue biopsy, pleural fluid, pericardial fluid, cerebral spinal fluid, peritoneal fluid, or any combination thereof.

In some embodiments, a method further comprises modifying the plurality of dsDNA fragments by performing an end-repairing procedure and an A-tailing procedure prior to ligating the loop-shaped adapters to the dsDNA fragments. In some embodiments, the loop-shaped adapters further comprise a sample-specific index sequence. In some embodiments, the loop-shaped adapters further comprise a universal priming site. In some embodiments, the loop-shaped adapters further comprise one or more sequencing oligonucleotides for use in a cluster generation and/or a sequencing procedure.

In some embodiments, the consensus sequence comprises a sequence of nucleotide bases, wherein each nucleotide base is identified at a given position in the consensus sequence when a specific nucleotide base is present in a majority of the sequence reads of the family. In some embodiments, the consensus sequence comprises a sequence of nucleotide bases, wherein each nucleotide base is identified at a given position in the consensus sequence when a specific nucleotide base is present in at least 80% of the sequence reads comprising the family. In some embodiments, the consensus sequence comprises a sequence of nucleotide bases, wherein each nucleotide base is identified at a given position in the consensus sequence when a specific nucleotide base is present in at least 90% of the sequence reads comprising the family. In some embodiments, the consensus sequence comprises a sequence of nucleotide bases, wherein each nucleotide base is identified at a given position in the consensus sequence when a specific nucleotide base is present in at least 95% of the sequence reads comprising the family.

In some embodiments, a method further comprises loading at least a portion of the sequencing library into a sequencing flow cell and generating a plurality of sequencing clusters on the flow cell, wherein each of the sequencing clusters comprises the forward strand and the reverse complement strand.

In some embodiments, the sequence reads are obtained from a next-generation sequencing (NGS) procedure. In some embodiments, the sequence reads are obtained from massively parallel sequencing using a sequencing-by-synthesis procedure. In some embodiments, the sequence reads are obtained from a paired-end sequencing procedure. In some embodiments, the sequence reads comprise a read pair, wherein each read pair comprises a first read of the forward strand and a second read of the reverse complement strand.

In some embodiments, a method further comprises using the one or more rare variants to detect a presence or absence of cancer, determine cancer status, monitor cancer progression, and/or determine a cancer classification. In some embodiments, monitoring cancer progression further comprises monitoring disease progression, monitoring therapy, or monitoring cancer growth. In some embodiments, the cancer classification further comprises determining cancer type and/or cancer tissue of origin. In some embodiments, monitoring cancer progression further comprises monitoring disease progression, monitoring therapy, or monitoring cancer growth.

In some embodiments, the cancer comprises a carcinoma, a sarcoma, a myeloma, a leukemia, a lymphoma, a blastoma, a germ cell tumor, or any combination thereof.

DEFINITIONS

Figure 1:
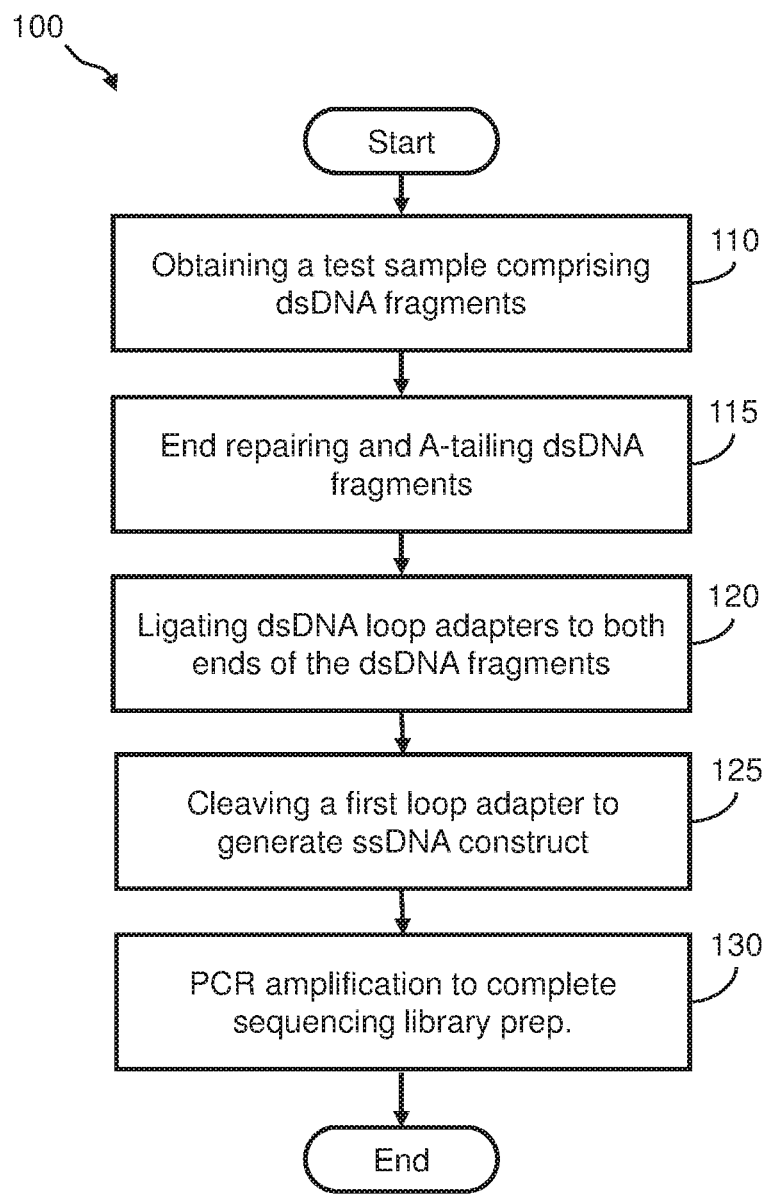
FIG. 1 is a flow diagram illustrating a method for preparing a sequencing library, in accordance with one embodiment of the present invention.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit, unless the context clearly dictates otherwise, between the upper and lower limit of that range and any other stated or intervening value in that stated range is encompassed within the invention. The upper and lower limits of these smaller ranges may independently be included in the smaller ranges encompassed within the invention, subject to any specifically excluded limit in the stated range.

Unless defined otherwise, technical and scientific terms used herein have the same meaning as commonly understood by one of ordinary skill in the art to which this invention belongs. Singleton et al., *Dictionary of Microbiology and Molecular Biology* 2nd ed., J. Wiley & Sons (New York, N.Y. 1994), provides one skilled in the art with a general guide to many of the terms used in the present application, as do the following, each of which is incorporated by reference herein in its entirety: Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Abbas et al, Cellular and Molecular Immunology, $6^{th}$ edition (Saunders, 2007).

All publications mentioned herein are expressly incorporated herein by reference to disclose and describe the methods and/or materials in connection with which the publications are cited.

The term "amplicon" as used herein means the product of a polynucleotide amplification reaction; that is, a clonal population of polynucleotides, which may be single stranded or double stranded, which are replicated from one or more starting sequences. The one or more starting sequences may be one or more copies of the same sequence, or they may be a mixture of different sequences. Preferably, amplicons are formed by the amplification of a single starting sequence. Amplicons may be produced by a variety of amplification reactions whose products comprise replicates of the one or more starting, or target, nucleic acids. In one aspect, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase, or oligonucleotide ligations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references, each of which are incorporated herein by reference herein in their entirety: Mullis et al, U.S. Pat. Nos. 4,683,195; 4,965,188; 4,683,202; 4,800,159 (PCR); Gelfand et al, U.S. Pat. No. 5,210,015 (real-time PCR with "taqman" probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japanese patent publ. JP 4-262799 (rolling circle amplification); and the like. In one aspect, amplicons of the invention are produced by PCRs. An amplification reaction may be a "real-time" amplification if a detection chemistry is available that permits a reaction product to be measured as the amplification reaction progresses, e.g., "real-time PCR", or "real-time NASBA" as described in Leone et al, Nucleic Acids Research, 26: 2150-2155 (1998), and like references.

As used herein, the term "amplifying" means performing an amplification reaction. A "reaction mixture" means a solution containing all the necessary reactants for performing a reaction, which may include, but is not be limited to, buffering agents to maintain pH at a selected level during a reaction, salts, co-factors, scavengers, and the like.

The terms "fragment" or "segment", as used interchangeably herein, refer to a portion of a larger polynucleotide molecule. A polynucleotide, for example, can be broken up, or fragmented into, a plurality of segments, either through natural processes, as is the case with, e.g., cfDNA fragments that can naturally occur within a biological sample, or through in vitro manipulation. Various methods of fragmenting nucleic acids are well known in the art. These methods may be, for example, either chemical or physical or enzymatic in nature. Enzymatic fragmentation may include partial degradation with a DNase; partial depurination with acid; the use of restriction enzymes; intron-encoded endonucleases; DNA-based cleavage methods, such as triplex and hybrid formation methods, that rely on the specific hybridization of a nucleic acid segment to localize a cleavage agent to a specific location in the nucleic acid molecule; or other enzymes or compounds which cleave a polynucleotide at known or unknown locations. Physical fragmentation methods may involve subjecting a polynucleotide to a high shear rate. High shear rates may be produced, for example, by moving DNA through a chamber or channel with pits or spikes, or forcing a DNA sample through a restricted size flow passage, e.g., an aperture having a cross sectional dimension in the micron or submicron range. Other physical methods include sonication and nebulization. Combinations of physical and chemical fragmentation methods may likewise be employed, such as fragmentation by heat and ion-mediated hydrolysis. See, e.g., Sambrook et al., "Molecular Cloning: A Laboratory Manual," 3rd Ed. Cold Spring Harbor Laboratory Press, Cold Spring Harbor, N.Y. (2001) ("Sambrook et al.) which is incorporated herein by reference for all purposes. These methods can be optimized to digest a nucleic acid into fragments of a selected size range.

The terms "polymerase chain reaction" or "PCR", as used interchangeably herein, mean a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors that are well-known to those of ordinary skill in the art, e.g., exemplified by the following references: McPherson et al, editors, PCR: A Practical Approach and PCR 2: A Practical Approach (IRL Press, Oxford, 1991 and 1995, respectively). For example, in a conventional PCR using Taq DNA polymerase, a double stranded target nucleic acid may be denatured at a temperature$>90°$ C., primers annealed at a temperature in the range 50-75° C., and primers extended at a temperature in the range 72-78° C. The term "PCR" encompasses derivative forms of the reaction, including, but not limited to, RT-PCR, real-time PCR, nested PCR, quantitative PCR, multiplexed PCR, and the like. The particular format of PCR being employed is discernible by one skilled in the art from the context of an application. Reaction volumes can range from a few hundred nanoliters, e.g., 200 nL, to a few hundred μL, e.g., 200 μL. "Reverse transcription PCR," or "RT-PCR," means a PCR that is preceded by a reverse transcription reaction that converts a target RNA to a complementary single stranded DNA, which is then amplified, an example of which is described in Tecott et al, U.S. Pat. No. 5,168,038, the disclosure of which is incorporated herein by reference in its entirety. "Real-time PCR" means a PCR for which the amount of reaction product, i.e., amplicon, is monitored as the reaction proceeds. There are many forms of real-time PCR that differ mainly in the detection chemistries used for monitoring the reaction product, e.g., Gelfand et al, U.S. Pat. No. 5,210,015 ("taqman"); Wittwer et al, U.S. Pat. Nos. 6,174,670 and 6,569,627 (intercalating dyes); Tyagi et al, U.S. Pat. No. 5,925,517 (molecular beacons); the disclosures of which are hereby incorporated by reference herein in their entireties. Detection chemistries for real-time PCR are reviewed in Mackay et al, Nucleic Acids Research, 30: 1292-1305 (2002), which is also incorporated herein by reference. "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Asymmetric PCR" means a PCR wherein one of the two primers employed is in great excess concentration so that the reaction is primarily a linear amplification in which one of the two strands of a target nucleic acid is preferentially copied. The excess concentration of asymmetric PCR primers may be expressed as a concentration ratio. Typical ratios are in the range of from 10 to 100. "Multiplexed PCR" means a PCR wherein multiple target sequences (or a single target sequence and one or more reference sequences) are simultaneously carried out in the same reaction mixture, e.g., Bernard et al, Anal. Biochem., 273: 221-228 (1999)(two-color real-time PCR). Usually, distinct sets of primers are employed for each sequence being amplified. Typically, the number of target sequences in a multiplex PCR is in the range of from 2 to 50, or from 2 to 40, or from 2 to 30. "Quantitative PCR" means a PCR designed to measure the abundance of one or more specific target sequences in a sample or specimen. Quantitative PCR includes both absolute quantitation and relative quantitation of such target sequences. Quantitative measurements are made using one or more reference sequences or internal standards that may be assayed separately or together with a target sequence. The reference sequence may be endogenous or exogenous to a sample or specimen, and in the latter case, may comprise one or more competitor templates. Typical endogenous reference sequences include segments of transcripts of the following genes: β-actin, GAPDH, $β_2$-microglobulin, ribosomal RNA, and the like. Techniques for quantitative PCR are well-known to those of ordinary skill in the art, as exemplified in the following references, which are incorporated by reference herein in their entireties: Freeman et al, Biotechniques, 26: 112-126 (1999); Becker-Andre et al, Nucleic Acids Research, 17: 9437-9447 (1989); Zimmerman et al, Biotechniques, 21: 268-279 (1996); Diviacco et al, Gene, 122: 3013-3020 (1992); and Becker-Andre et al, Nucleic Acids Research, 17: 9437-9446 (1989).

The term "primer" as used herein means an oligonucleotide, either natural or synthetic, that is capable, upon forming a duplex with a polynucleotide template, of acting as a point of initiation of nucleic acid synthesis and being extended from its 3'-end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually, primers are extended by a DNA polymerase. Primers usually have a length in the range of from 14 to 40 nucleotides, or in the range of from 18 to 36 nucleotides. Primers are employed in a variety of nucleic acid amplification reactions, for example, linear amplification reactions using a single primer, or polymerase chain reactions, employing two or more primers. Guidance for selecting the lengths and sequences of primers for particular applications is well known to those of ordinary skill in the art, as evidenced by the following reference that is incorporated by reference herein in its entirety: Dieffenbach, editor, PCR Primer: A Laboratory Manual, $2^{nd}$ Edition (Cold Spring Harbor Press, New York, 2003).

The terms "unique sequence tag", "sequence tag", "tag" or "barcode", as used interchangeably herein, refer to an oligonucleotide that is attached to a polynucleotide or template molecule and is used to identify and/or track the polynucleotide or template in a reaction or a series of reactions. A sequence tag may be attached to the 3'- or 5'-end of a polynucleotide or template, or it may be inserted into the interior of such polynucleotide or template to form a linear conjugate, sometimes referred to herein as a "tagged polynucleotide," or "tagged template," or the like. Sequence tags may vary widely in size and compositions; the following references, which are incorporated herein by reference in their entireties, provide guidance for selecting sets of sequence tags appropriate for particular embodiments: Brenner, U.S. Pat. No. 5,635,400; Brenner and Macevicz, U.S. Pat. No. 7,537,897; Brenner et al, Proc. Natl. Acad. Sci., 97: 1665-1670 (2000); Church et al, European patent publication 0 303 459; Shoemaker et al, Nature Genetics, 14: 450-456 (1996); Morris et al, European patent publication 0799897A1; Wallace, U.S. Pat. No. 5,981,179; and the like. Lengths and compositions of sequence tags can vary widely, and the selection of particular lengths and/or compositions depends on several factors including, without limitation, how tags are used to generate a readout, e.g., via a hybridization reaction or via an enzymatic reaction, such as sequencing; whether they are labeled, e.g., with a fluorescent dye or the like; the number of distinguishable oligonucleotide tags required to unambiguously identify a set of polynucleotides, and the like, and how different the tags of a particular set must be in order to ensure reliable identification, e.g., freedom from cross hybridization or misidentification from sequencing errors. In one aspect, sequence tags can each have a length within a range of from about 2 to about 36 nucleotides, or from about 4 to about 30 nucleotides, or from about 4 to about 20 nucleotides, or from about 8 to about 20 nucleotides, or from about 6 to about 10 nucleotides. In one aspect, sets of sequence tags are used, wherein each sequence tag of a set has a unique nucleotide sequence that differs from that of every other tag of the same set by at least two bases; in another aspect, sets of sequence tags are used wherein the sequence of each tag of a set differs from that of every other tag of the same set by at least three bases. In some embodiments, the unique sequence tag can be a "unique molecular identifier", or "UMI," and can be used, for example, to differentiate various unique nucleic acid sequence fragments originating from a test sample. In other embodiments, a "sequence tag" can be used to differentiate nucleic acid sequence fragments that originate from different test samples (e.g., a sample-specific sequence tag).

The terms "subject" and "patient" are used interchangeably herein and refer to a human or non-human animal who is known to have, or potentially has, a medical condition or disorder, such as, e.g., a cancer.

The term "sequence read" as used herein refers to a nucleotide sequence obtained from or read from a nucleic acid obtained from a subject. Sequence reads can be obtained through various methods known in the art. Generally, sequence reads are obtained post-amplification (e.g., polymerase chain reaction, such as bridge amplification) of a nucleic acid fragment that is obtained or enriched from a test sample.

The term "cell free nucleic acid," "cell free DNA," or "cfDNA," "cell-free RNA," or "cfRNA," refers to nucleic acid fragments that circulate in an individual's body (e.g., in a body fluid such as the bloodstream) and originate from one or more healthy cells and/or from one or more diseased cells (e.g., cancer cells).

The terms "circulating tumor DNA" or "ctDNA" and "circulating tumor RNA" or "ctRNA" refer to nucleic acid fragments (DNA or RNA) that originate from tumor cells or other types of cancer cells, which can be released into a subject's bloodstream as a result of biological processes, such as apoptosis or necrosis of dying cells, or can be actively released by viable tumor cells.

DETAILED DESCRIPTION OF THE INVENTION

Aspects of the invention include methods for preparing sequencing libraries, performing sequencing procedures that can correct for process-related errors, and identifying rare variants that are or may be indicative of cancer. In some aspects, methods for preparing an improved sequencing library from a test sample containing a plurality of double-strand DNA (dsDNA) molecules or fragments are provided. In some embodiments, a sequencing library can be used to obtain duplex sequencing data or sequence reads, for comparison of sequencing data or sequence reads of a forward strand and a reverse complement strand. In some embodiments, the forward strand and the reverse complement strand can be compared to generate a consensus sequence, and the consensus sequence used for error correction. In some embodiments, the forward strand and the reverse complement strand can be compared to generate a consensus sequence, and the consensus sequence used for identifying a rare variant or mutation. In some embodiments, the identified rare variant or mutation can be used for detecting the presence or absence of cancer, determining cancer status, monitoring cancer progression, and/or determining a cancer classification (e.g., a cancer type and/or tissue of origin).

FIG. 1 is a flow diagram illustrating a method 100 for preparing a sequencing library from a test sample that comprises dsDNA. As noted above, in certain embodiments, the sequencing library can be used for duplex sequencing. As shown in FIG. 1, at step 110, a biological test sample is obtained from a subject (e.g., a patient). In one embodiment, the biological sample can be a sample selected from the group consisting of blood, plasma, serum, urine and saliva samples. In some embodiments, the sample is a plasma sample from a cancer patient, or a patient suspected of having cancer. Alternatively, the biological sample can comprise a sample selected from the group consisting of whole blood, a blood fraction, a tissue biopsy, pleural fluid, pericardial fluid, cerebral spinal fluid, and peritoneal fluid. In accordance with some embodiments, the biological test sample comprises a plurality of cell-free DNA (cfDNA) fragments. In other embodiments, the biological test sample comprises a plurality of cell-free DNA (cfDNA) fragments originating from healthy cells and from cancer cells. Optionally, in one embodiment, cell-free nucleic acids (e.g., cfDNA) can be extracted and/or purified from the biological test sample before proceeding with subsequent library preparation steps. In general, any method known in the art can be used to extract and purify cell-free nucleic acids from the biological test sample. For example, cell-free nucleic acids can be extracted and purified using one or more known commercially available protocols or kits, such as the QIAAMP® circulating nucleic acid kit (Qiagen).

At step 115, the double-strand DNA (dsDNA) fragments are modified for adapter ligation. For example, an end repair reaction can be performed to repair any overhanging ends and/or gaps in the double-stranded target nucleic acid molecules and the 5' ends of the molecules phosphorylated. In one embodiment, the ends of the dsDNA fragments are end repaired using, for example, T4 DNA polymerase and Klenow polymerase and phosphorylated with a polynucleotide kinase enzyme. A single "A" deoxynucleotide can then be added to both 3' ends of the target nucleic acid molecules, producing a single-base 3' A overhang.

At step 120, a set of loop-shaped adapters are ligated to the nucleic acid molecules to generate a plurality of adapter-ligated dsDNA products or constructs. In one embodiment, the set of loop-shaped adapters comprises a plurality of first and second loop-shaped adapters. For example, the loop-shaped adapters can comprise a plurality of first loop-shaped adapters, each comprising a unique molecular identifier (UMI) and an endonuclease restriction site and a second plurality of loop-shaped adapters, each optionally comprising a unique molecular identifier (UMI).

In accordance with the subject methods, the ligation reaction generates a mixture of adapter-ligated dsDNA products, i.e., fully ligated dsDNA molecules (with adapters ligated on both ends), partially ligated nucleic acid molecules (with an adapter ligated only on one end), and non-ligated nucleic molecules (with no adapters ligated). Only the fully ligated nucleic acid molecules with adapters on both ends are suitable for sequencing. The fully ligated dsDNA molecules can result in the formation of one of three possible unique circular-shaped constructs: a first construct comprising a first adapter and a second adapter ligated on opposite ends of the dsDNA molecule (e.g., first adapter-dsDNA-second adapter); a second construct comprising two first adapters ligated on opposite ends of the dsDNA molecule (i.e., first adapter-dsDNA-first adapter); and a third construct comprising two second adapters ligated on opposite ends of the dsDNA molecule (i.e., second adapter-dsDNA-second adapter (see, for example, FIG. 2). In general, any known ligase can be used for ligation of the adapters to the double-stranded nucleic acid molecules. For example, in one embodiment, the ligation reaction is performed using a T4 DNA ligase. In another embodiment, the ligase used is a T7 DNA ligase.

In one embodiment, the loop-shaped adapters can include a unique molecular identifier (UMI) sequence, such that, after library preparation, the sequencing library will include UMI-tagged amplicons derived from cell-free nucleic acid fragments. In one embodiment, unique sequence tags (e.g., unique molecular identifiers (UMIs)) can be used to identify unique nucleic acid sequences from a cell-free nucleic acid sample. For example, differing unique sequence tags (UMIs) can be used to differentiate various unique nucleic acid sequence fragments originating from the test sample. In another embodiment, unique sequence tags (UMIs) can be used to reduce amplification bias, which is the asymmetric amplification of different targets due to differences in nucleic acid composition (e.g., high GC content). The unique sequence tags (UMIs) can also be used to discriminate between nucleic acid mutations that arise during amplification. The unique sequence tags can be present in a multi-functional nucleic acid sequencing adapter, which sequencing adapter can comprise both a unique sequence tag and a universal priming site. In one embodiment, the unique sequence tag can comprise a short oligonucleotide sequence having a length of from about 2 nt to about 100 nt, such as from about 2 nt to about 60 nt, such as from about 2 to about 40 nt, or such as from about 2 to about 20 nt. In another embodiment, the UMI tag can comprise a short oligonucleotide sequence greater than about 5, 6, 7, 8, 9, 10, 11, 12, 13, 14, 15, 16, 17, or 18 nucleotides (nt) in length.

In other embodiments, the sequencing adapters can comprise a universal primer and/or one or more sequencing oligonucleotides for use in subsequent cluster generation and/or sequencing (e.g., known P5 and P7 sequences for use in sequencing by synthesis (SBS) (Illumina, San Diego, Calif.)).

At step 125, the first loop-shaped adapters are cleaved with a site-specific restriction endonuclease. As noted above, the fully ligated dsDNA molecules can result in the formation of one of three possible unique circular-shaped constructs: a first construct comprising a first and second adapter ligated on opposite ends of a dsDNA molecule (e.g., first adapter-dsDNA-second adapter); a second construct comprising two first adapters ligated on opposite ends of a dsDNA molecule (i.e., first adapter-dsDNA-first adapter); and a third construct comprising two second adapters ligated on opposite ends of a dsDNA molecule (i.e., second adapter-dsDNA-second adapter) (see, for example, FIG. 2). Cleavage of the first loop-shaped adapters contained in the first construct (e.g., first adapter-dsDNA-second adapter) generates a plurality of linear single-stranded DNA (ssDNA) molecules comprising the forward strand and reverse complement strand from the original dsDNA molecules. These ssDNA molecule constructs (i.e., containing both the forward strand and reverse complement strand) allow for sequencing of both the forward and reverse complement strands in the same sequencing reaction (e.g., a single cluster on a sequencing flow cell). Cleavage of the first loop-shaped adapters contained in the second construct (i.e., first adapter-dsDNA-first adapter) results in a plurality of shorter ssDNA molecules comprising either the forward strand or the reverse complement strand from the dsDNA, but not both. The third construct (i.e., second adapter-dsDNA-second adapter) does not contain a site-specific restriction endonuclease, would be maintained as a circular-shaped construct, and would not be sequenced in any subsequent sequencing reaction. Finally, at step 130, the ssDNA molecules derived from cleavage of the circular-shaped constructs are PCR amplified to complete the sequencing library preparation.

Figure 2:
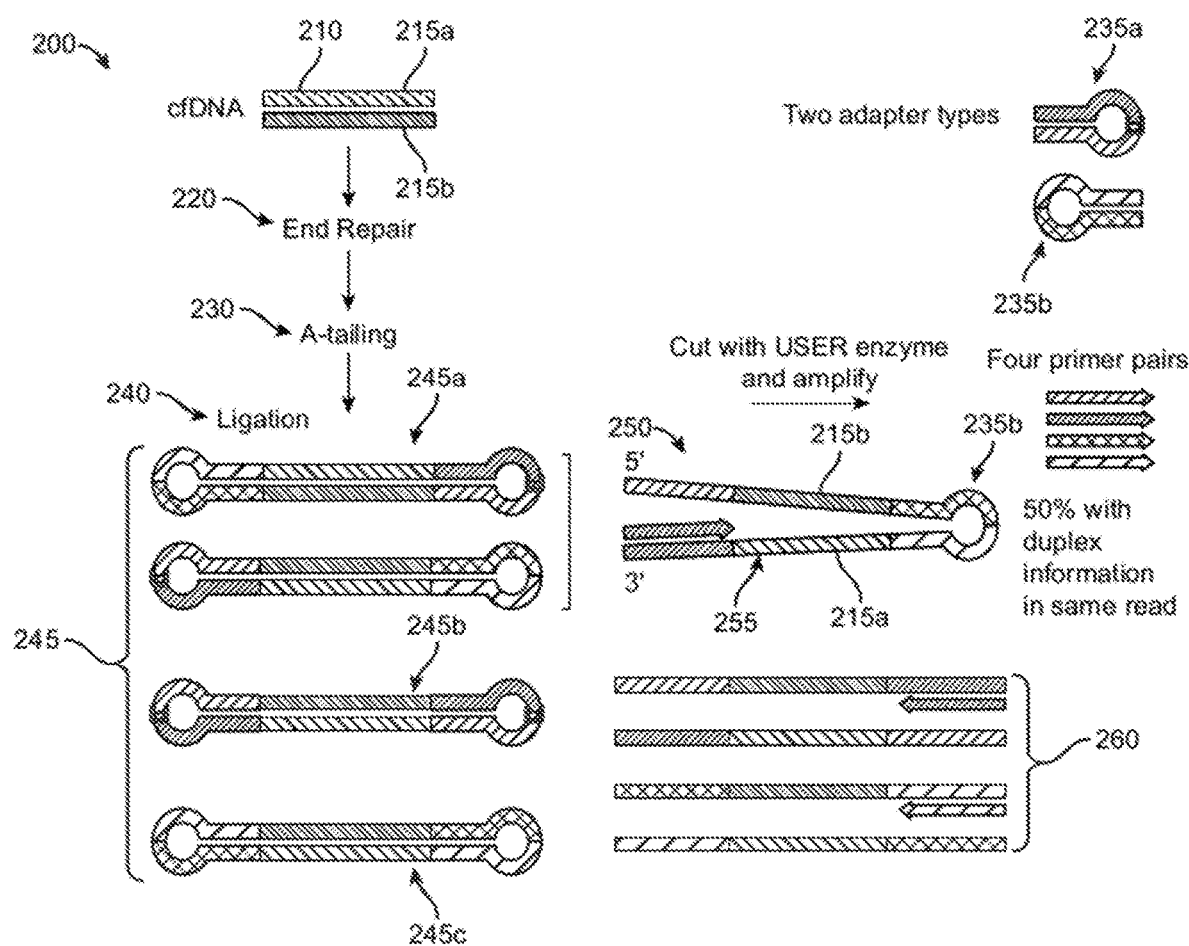
FIG. 2 is a schematic illustrating a method for preparing a sequencing library, in accordance with the method of FIG. 1.

FIG. 2 is an illustration showing pictorially the steps of a method 200 for preparing an improved sequencing library that can be used, for example, for duplex sequencing 200, as described above with reference to FIG. 1.

As shown in FIG. 2, a plurality of double-stranded DNA (dsDNA) fragments 210 are provided, wherein the dsDNA fragments 210 each comprise a forward strand 215a and a reverse complement strand 215b. As shown in FIG. 2, the dsDNA fragment 210 can be end-repaired, at step 220, and A-tailed, at step 230. Furthermore, as shown in FIG. 2, a plurality of first loop-shaped adapters 235a and a plurality of second loop-shaped adapters 235b are provided.

As shown at step 240, the first loop-shaped adapters 235a and second loop-shaped adapters 235b can be ligated to the end-repaired and A-tailed dsDNA fragments contained within a test sample, forming a plurality of fully ligated circular-shaped constructs 245. As shown in FIG. 2, three possible fully ligated unique circular-shaped constructs can be formed: a first construct 245a comprising a first and second adapter ligated on opposite ends of the dsDNA molecule (e.g., first adapter-dsDNA-second adapter); a second construct 245b comprising two first adapters ligated on opposite ends of the dsDNA molecule (i.e., first adapter-dsDNA-first adapter); and a third construct 245c comprising two second adapters ligated on opposite ends of the dsDNA molecule (i.e., second adapter-dsDNA-second adapter.

As shown at step 250, the first loop-shaped adapters are cleaved with a site-specific restriction endonuclease. As noted above, cleavage of the first loop-shaped adapters contained in the first construct 245a (e.g., first adapter-dsDNA-second adapter) generates a plurality of linear single-stranded DNA (ssDNA) molecules 255 comprising the forward strand and the reverse complement strand from the original dsDNA molecules. These ssDNA molecule constructs 255 include both the forward strand and reverse complement strands, allow for sequencing of both the forward and reverse complement strands in the same sequencing reaction (e.g., a single cluster on a sequencing flow cell). Cleavage of the first loop-shaped adapters contained in the second construct 245b (i.e., first adapter-dsDNA-first adapter) results in a plurality of shorter ssDNA molecules 260 comprising either the forward strand or the reverse complement strand from the dsDNA, but not both. The third construct 245c (i.e., second adapter-dsDNA-second adapter) does not contain a site-specific restriction endonuclease, is maintained as a circular-shaped construct, and cannot not be sequenced in any subsequent sequencing reaction.

Figure 3:
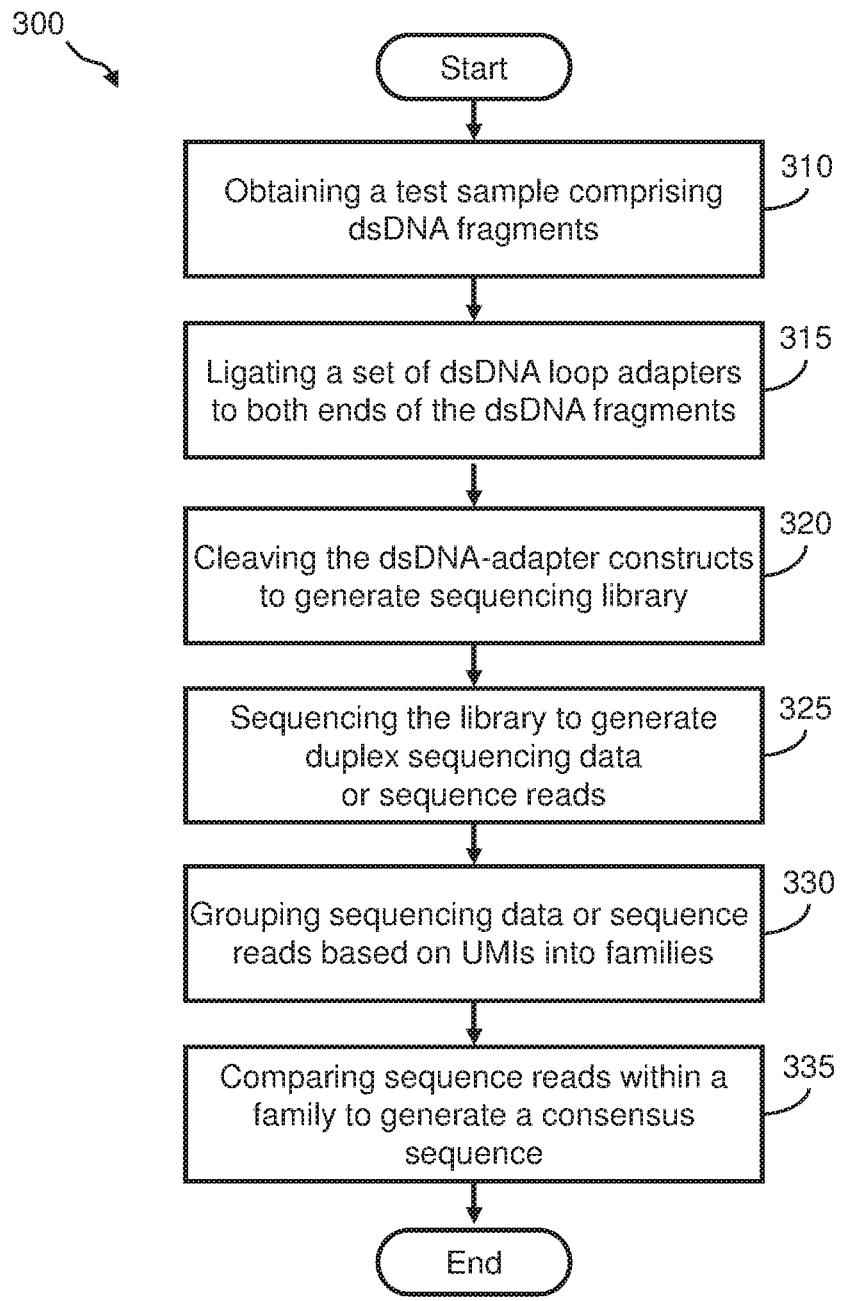
FIG. 3 is a flow diagram illustrating a method for error correction using a sequencing library prepared in accordance with the method of FIG. 1.

FIG. 3 is a flow diagram illustrating a method 300 for preparing an improved sequencing library for duplex sequencing based error correction.

As shown in FIG. 3, at step 310, a biological test sample is obtained from a subject (e.g., a patient) known to have or suspected of having cancer. As discussed in more detail elsewhere herein, the biological sample can comprise blood, plasma, serum, urine or saliva. In some embodiments, the sample is a plasma sample from a cancer patient, or a patient suspected of having cancer. Alternatively, as noted herein, the biological sample can comprise whole blood, a blood fraction, a tissue biopsy, a pleural fluid, pericardial fluid, a cerebral spinal fluid, or a peritoneal fluid. In accordance with some embodiments, the biological test sample can comprise a plurality of cell-free nucleic acid (e.g., cell-free DNA (cfDNA)) fragments. Optionally, the cell-free nucleic acids (e.g., cfDNA) can be extracted and/or purified from the biological test sample using any means known in the art.

At step 315, the cell-free nucleic acid sample (e.g., cfDNA) is used to prepare a sequencing library. In general, any method known in the art for preparing a sequencing library can be used. For example, a standard sequencing library preparation protocol (e.g., TruSeq® library preparation protocol (Illumina, Inc.)) that includes the steps of end repairing, 3' A-tailing, and adapter ligation can be used. However, in accordance with some embodiments, as disclosed in more detail elsewhere herein, a set of loop-shaped adapters comprising a plurality of first and second loop-shaped adapters are used in conjunction with the subject methods. For example, the loop-shaped adapters can comprise a plurality of first loop-shaped adapters comprising a unique molecular identifier (UMI) and an endonuclease restriction site and a second plurality of loop-shaped adapters optionally comprising a unique molecular identifier (UMI). Furthermore, as noted elsewhere in this disclosure, the loop-shaped adapters can also include one or more universal primers and/or one or more sequencing oligonucleotides for use in subsequent cluster generation and/or sequencing (e.g., known P5 and P7 sequences for used in sequencing by synthesis (SBS) (Illumina, San Diego, Calif.)).

As previously described, the ligation reaction generates a mixture of adapter-ligated dsDNA products, i.e., fully ligated dsDNA molecules (with adapters ligated on both ends), partially ligated nucleic acid molecules (with an adapter ligated only on one end), and non-ligated nucleic molecules (with no adapters ligated). Only the fully ligated nucleic acid molecules with adapters on both ends are suitable for sequencing. The fully ligated dsDNA molecules can result in the formation three unique circular-shaped constructs: a first construct comprising the first and second adapter ligated on opposite ends of the dsDNA molecule (e.g., first adapter-dsDNA-second adapter); a second construct comprising two first adapters ligated on opposite ends of the dsDNA molecule (i.e., first adapter-dsDNA-first adapter); and a third construct comprising two second adapters ligated on opposite ends of the dsDNA molecule (i.e., second adapter-dsDNA-second adapter (see, for example, FIG. 2). In general, any known ligase can be used for ligation of the adapters to the double-stranded nucleic acid molecules. For example, in one embodiment, the ligation reaction is performed using a T4 DNA ligase. In another embodiment, the ligase used is a T7 DNA ligase.

At step 320, the first loop-shaped adapters are cleaved with a site-specific restriction endonuclease. As noted above, the fully ligated dsDNA molecules can result in the formation of one of three possible unique circular-shaped constructs: a first construct comprising a first adapter and second adapter ligated on opposite ends of a dsDNA molecule (e.g., first adapter-dsDNA-second adapter); a second construct comprising two first adapters ligated on opposite ends of a dsDNA molecule (i.e., first adapter-dsDNA-first adapter); and a third construct comprising two second adapters ligated on opposite ends of a dsDNA molecule (i.e., second adapter-dsDNA-second adapter) (see, for example, FIG. 2). Cleavage of the first loop-shaped adapters contained in the first construct (e.g., first adapter-dsDNA-second adapter) generates a plurality of linear single-stranded DNA (ssDNA) molecules comprising the forward strand and reverse complement strand from the original dsDNA molecules. These ssDNA molecule constructs (i.e., containing both the forward strand and reverse complement strand) allow for sequencing of both the forward and reverse complement strands in the same sequencing reaction (e.g., a single cluster on a sequencing flow cell). Cleavage of the first loop-shaped adapters contained in the second construct (i.e., first adapter-dsDNA-first adapter) results in a plurality of shorter ssDNA molecules comprising either the forward strand or the reverse complement strand from the dsDNA, but not both. The third construct (i.e., second adapter-dsDNA-second adapter) does not contain a site-specific restriction endonuclease, would be maintained as a circular-shaped construct, and would not be sequenced in any subsequent sequencing reaction. Optionally, the ssDNA molecules can be PCR amplified to complete sequencing library preparation.

At step 325, at least a portion of the sequencing library prepared in step 320 is sequenced to obtain sequencing data or sequence reads. In general, any method known in the art can be used to obtain sequence data or sequence reads from the sequencing library. For example, in one embodiment, sequencing data or sequence reads from the sequencing library can be acquired using next generation sequencing (NGS). Next-generation sequencing methods include, for example, sequencing by synthesis technology (Illumina), pyrosequencing (454), ion semiconductor technology (Ion Torrent sequencing), single-molecule real-time sequencing (Pacific Biosciences), sequencing by ligation (SOLiD sequencing), and nanopore sequencing (Oxford Nanopore Technologies). In some embodiments, sequencing is massively parallel sequencing using sequencing-by-synthesis with reversible dye terminators. In other embodiments, sequencing is sequencing-by-ligation. In yet other embodiments, sequencing is single molecule sequencing. In still another embodiment, sequencing is paired-end sequencing. Optionally, an amplification step can be performed prior to sequencing. In accordance with embodiments of the subject methods, cleavage of the first loop-shaped adapters contained in the first construct (e.g., first adapter-dsDNA-second adapter) generates a plurality of linear single-stranded DNA (ssDNA) molecules comprising the forward strand and reverse complement strand from the original dsDNA molecules. These ssDNA molecule constructs (i.e., containing both the forward strand and reverse complement strand) allow for sequencing of both the forward and reverse complement strands in the same sequencing reaction (e.g., a single cluster on a sequencing flow cell), thereby simplifying identification of the associated forward strand and reverse complement strand from an original dsDNA fragment from the test sample.

As shown in FIG. 3, at step 330, sequencing data or sequence reads are grouped into families based on their unique molecular identifiers (UMIs). As used herein, a "family group" comprises a plurality of sequence reads identified, based on their associated UMIs, as originating from a single double-strand DNA (dsDNA) molecule from the test sample. A "family" of sequence reads, as used herein, includes both a set of sequence reads originating from a specific forward strand and a set of sequence reads originating from the reverse complement strand (i.e., the forward strand and reverse complement from a single dsDNA molecule). For example, a family of sequence reads can be placed into a family group, where each of the sequence reads has either the same UMI (e.g., on a set of forward strands), or the reverse complement of the UMI sequence (e.g., on a set of reverse complement strands).

At step 335, the sequence reads within a family are compared to generate a consensus sequence. For example, the nucleotide base sequence for each of the plurality of sequence reads in a family (originating from both the forward strands and reverse complement strands) can be compared to determine the most probable nucleotide base at each position along the sequence. As used herein, a "consensus sequence" comprises a sequence of nucleotide bases identified as the most probable at each position along the sequence. In one embodiment, the consensus sequence comprises a sequence of nucleotide bases, wherein each base is identified as the most probable nucleotide base at a given position when a specific base is present at the position in a majority of the sequence reads within a family (i.e., from a plurality of sequence reads derived from both the forward and reverse complement strands within a family). In other embodiments, the consensus sequence comprises a sequence of nucleotide bases, wherein each base is identified as the most probable nucleotide base at a given position when a specific base is present at the position in at least 60%, at least 70%, at least 80%, at least 90%, or at least 95%, of the family members. In accordance with one embodiment, errors introduced during sample preparation and sequencing can be identified, and eliminated through the generation of a consensus sequence.

Figure 4:
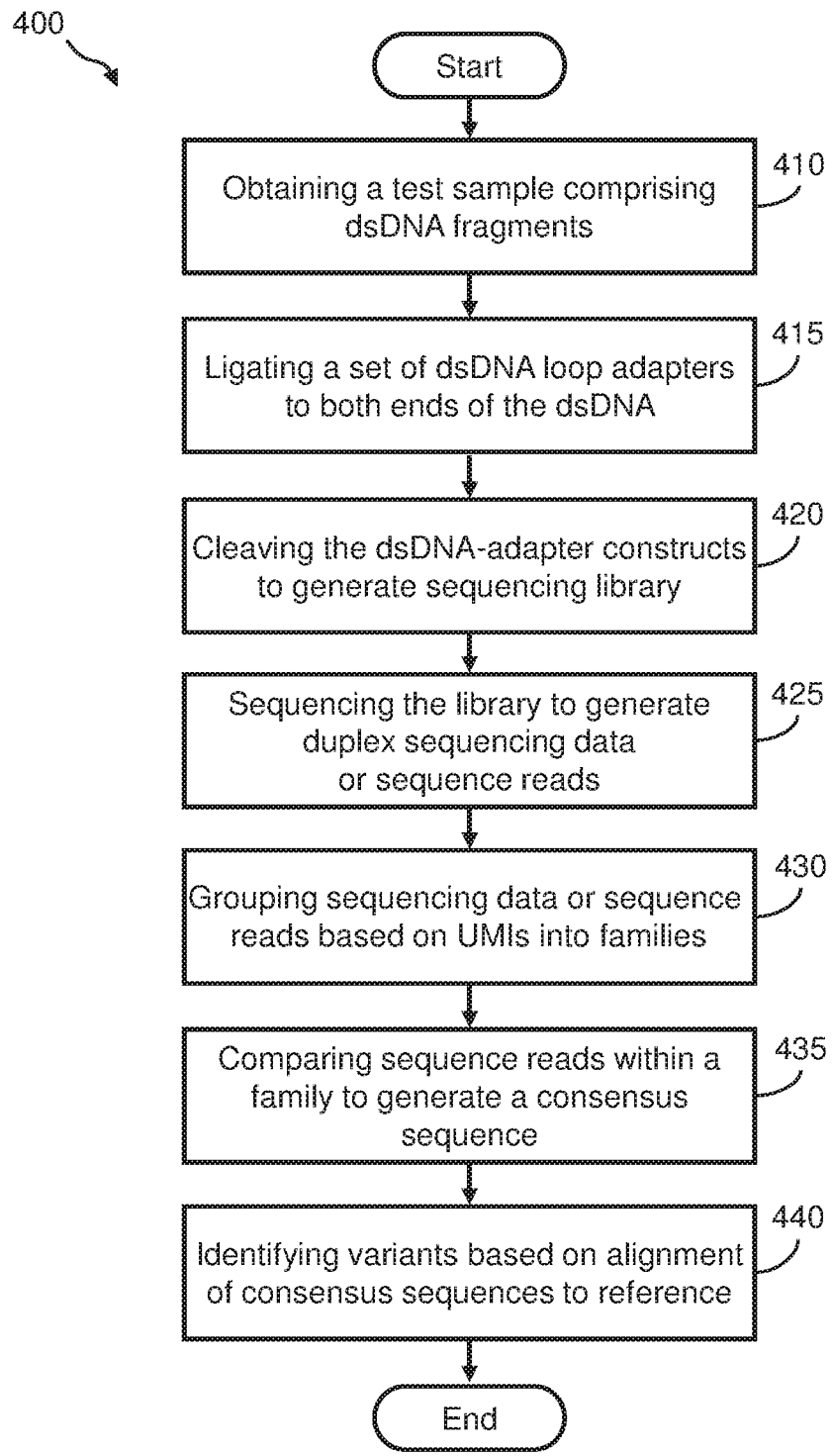
FIG. 4 is a flow diagram illustrating a method for variant detection, using a sequencing library prepared in accordance with the method of FIG. 1.

FIG. 4 is a flow diagram illustrating a method 400 for preparing an improved sequencing library for duplex sequencing-based rare variant detection.

As shown in FIG. 4, at step 410, a biological test sample is obtained from a subject (e.g., a patient) known to have or suspected of having cancer. As discussed in more detail elsewhere herein, the biological sample can comprise blood, plasma, serum, urine or saliva. In some embodiments, the sample is a plasma sample from a cancer patient, or a patient suspected of having cancer. Alternatively, as noted above, the biological sample can comprise whole blood, a blood fraction, a tissue biopsy, a pleural fluid, pericardial fluid, a cerebral spinal fluid, or a peritoneal fluid. In accordance with some embodiments, the biological test sample can comprise a plurality of cell-free nucleic acids (e.g., cell-free DNA (cfDNA)) fragments. Optionally, the cell-free nucleic acids (e.g., cfDNA) can be extracted and/or purified from the biological test sample using any means known in the art.

At step 415 the cell-free nucleic acid sample (e.g., cfDNA) is used to prepare a sequencing library. In general, any method known in the art for preparing a sequencing library can be used. For example, a standard sequencing library preparation protocol (e.g., TRUSEQ® library preparation protocol (Illumina, Inc.)) that includes the steps of end repairing, 3' A-tailing, and adapter ligation can be used. However, in accordance with embodiments of the subject methods, as disclosed in more detail elsewhere herein, a set of loop-shaped adapters comprising a plurality of first and second loop-shaped adapters can be used. For example, the loop-shaped adapters can comprise a plurality of first loop-shaped adapters comprising a unique molecular identifier (UMI) and an endonuclease restriction site and a second plurality of loop-shaped adapters optionally comprising a unique molecular identifier (UMI). Furthermore, as noted elsewhere in this disclosure, the loop-shaped adapters can also include one or more universal primers and/or one or more sequencing oligonucleotides for use in subsequent cluster generation and/or sequencing (e.g., known P5 and P7 sequences for used in sequencing by synthesis (SBS) (Illumina, San Diego, Calif.)).

As previously described, in some embodiments, the ligation reaction generates a mixture of adapter-ligated dsDNA products, i.e., fully ligated dsDNA molecules (with adapters ligated on both ends), partially ligated nucleic acid molecules (with an adapter ligated only on one end), and non-ligated nucleic acid molecules (with no adapters ligated). Only the fully ligated nucleic acid molecules with adapters on both ends are suitable for sequencing. The fully ligated dsDNA molecules can result in the formation of one of three possible unique circular-shaped constructs: a first construct comprising a first and second adapter ligated on opposite ends of the dsDNA molecule (e.g., first adapter-dsDNA-second adapter); a second construct comprising two first adapters ligated on opposite ends of the dsDNA molecule (i.e., first adapter-dsDNA-first adapter); and a third construct comprising two second adapters ligated on opposite ends of the dsDNA molecule (i.e., second adapter-dsDNA-second adapter (see, for example, FIG. 2). In general, any known ligase can be used for ligation of the adapters to the double-stranded nucleic acid molecules. For example, in one embodiment, the ligation reaction is performed using a T4 DNA ligase. In another embodiment, the ligase used is a T7 DNA ligase.

At step 420, the first loop-shaped adapters are cleaved with a site-specific restriction endonuclease. Cleavage of the first loop-shaped adapters contained in the first construct (e.g., first adapter-dsDNA-second adapter) generates a plurality of linear single-stranded DNA (ssDNA) molecules comprising the forward strand and reverse complement strand from the original dsDNA molecules. These ssDNA molecule constructs (i.e., containing both the forward strand and reverse complement strand) allow for sequencing of both the forward and reverse complement strands in the same sequencing reaction (e.g., from a single cluster on a sequencing flow cell). Cleavage of the first loop-shaped adapters contained in the second construct (i.e., first adapter-dsDNA-first adapter) results in a plurality of shorter ssDNA molecules comprising either the forward strand or the reverse complement strand from the dsDNA, but not both. The third construct (i.e., second adapter-dsDNA-second adapter) does not contain a site-specific restriction endonuclease, would be maintained as a circular-shaped construct, and would not be sequenced in any subsequent sequencing reaction. Optionally, the ssDNA molecules can be PCR amplified to complete sequencing library preparation.

At step 425, at least a portion of the sequencing library prepared in step 420 is sequenced to obtain sequencing data or sequence reads. In general, any method known in the art can be used to obtain sequence data or sequence reads from the sequencing library. For example, in one embodiment, sequencing data or sequence reads from the sequencing library can be acquired using next generation sequencing (NGS). Next-generation sequencing methods include, for example, sequencing by synthesis technology (Illumina), pyrosequencing (454), ion semiconductor technology (Ion Torrent sequencing), single-molecule real-time sequencing (Pacific Biosciences), sequencing by ligation (SOLiD sequencing), and nanopore sequencing (Oxford Nanopore Technologies). In some embodiments, sequencing is massively parallel sequencing using sequencing-by-synthesis with reversible dye terminators. In other embodiments, sequencing is sequencing-by-ligation. In yet other embodiments, sequencing is single molecule sequencing. In still another embodiment, sequencing is paired-end sequencing. Optionally, an amplification step can be performed prior to sequencing. In accordance with some embodiments, cleavage of the first loop-shaped adapters contained in the first construct (e.g., first adapter-dsDNA-second adapter) generates a plurality of linear single-stranded DNA (ssDNA) molecules comprising the forward strand and reverse complement strand from the original dsDNA molecules. These ssDNA molecule constructs (i.e., containing both the forward strand and reverse complement strand) allow for sequencing of both the forward and reverse complement strands in the same sequencing reaction (e.g., a single cluster on a sequencing flow cell), thereby simplifying identification of the associated forward strand and reverse complement strand from an original dsDNA fragment from the test sample.

As shown in FIG. 4, at step 430, sequencing data or sequence reads are grouped into families based on their unique molecular identifiers (UMIs). As used herein, a "family group" comprises a plurality of sequence reads identified, based on their associated UMIs, as originating from a single double-strand DNA (dsDNA) molecule from the test sample. A "family" of sequence reads, as used herein, includes both a set of sequence reads originating from a specific forward strand and a set of sequence reads originating from the reverse complement strand (i.e., the forward strand and reverse complement from a single dsDNA molecule). For example, a family of sequence reads can be placed into a family group, where each of the sequence reads has either the same UMI (e.g., on a set of forward strands), or the reverse complement of the UMI sequence (e.g., on a set of reverse complement strands).

At step 435, the sequence reads within a family are compared to generate a consensus sequence. For example, the nucleotide base sequence for each of the plurality of sequence reads in a family (originating from both the forward strands and reverse complement strands) can be compared to determine the most probable nucleotide base at each position along the sequence. As used herein, a "consensus sequence" comprises a sequence of nucleotide bases identified as the most probable at each position along the sequence. In one embodiment, the consensus sequence comprises a sequence of nucleotide bases, wherein each base is identified as the most probable nucleotide base at a given position when a specific base is present at the position in a majority of the sequence reads within a family (i.e., from a plurality of sequence reads derived from both the forward and reverse complement strands within a family). In other embodiments, the consensus sequence comprises a sequence of nucleotide bases, wherein each base is identified as the most probable nucleotide base at a given position when a specific base is present at the position in at least about 60%, at least about 70%, at least about 80%, at least about 90%, or at least about 95% of the family members. In accordance with one embodiment, errors introduced during sample preparation and sequencing can be identified, and eliminated through the generation of a consensus sequence.

Finally, as shown at step 440, the consensus sequence can be compared to, or aligned to, a reference sequence to identify a rare variant or mutation. For example, a rare variant or mutation can be identified where the consensus sequence varies at one or more nucleotide base positions compared to the reference sequence. Rare variants and/or mutations may include, for example, genetic alterations such as a somatic point mutation(s) (e.g., single nucleotide variations (SNVs)), indels and/or a somatic copy number alteration(s) (sCNA; e.g., amplification(s) and/or deletion(s)). In some embodiments, the somatic point mutation(s) (e.g., single nucleotide variations (SNVs)) and/or a somatic copy number alteration(s) (sCNA; e.g., amplification(s) and/or deletion(s)) may be tumor-derived. In another embodiment, a rare variant or mutation can be identified based on de novo assembly of sequence reads within a family e.g., using De Bruijn graph assembly (not shown). In accordance with one embodiment, one or more rare variants and/or mutations identified can be used for detecting the presence or absence of cancer, determining cancer stage, monitoring cancer progression, and/or for determining a cancer classification (e.g., cancer type or cancer tissue of origin). In another embodiment, the sequencing data or sequence reads can be used to infer or predict the presence or absence of cancer, cancer status and/or a cancer classification.

In one embodiment, one or more rare variants and/or mutations can be analyzed to detect the presence or absence of, determine the stage of, monitor progression of, and/or classify a carcinoma, a sarcoma, a myeloma, a leukemia, a lymphoma, a blastoma, a germ cell tumor, or any combination thereof. In some embodiments, the carcinoma may be an adenocarcinoma. In other embodiments, the carcinoma may be a squamous cell carcinoma. In still other embodiments, the carcinoma is selected from the group consisting of: small cell lung, non-small-cell lung, nasopharyngeal, colorectal, anal, liver, urinary bladder, cervical, testicular, ovarian, gastric, esophageal, head-and-neck, pancreatic, prostate, renal, thyroid, melanoma, and breast carcinoma. In another embodiment, one or more rare variants and/or mutations can be analyzed to detect a presence or absence of, determine the stage of, monitor progression of, and/or classify a sarcoma. In certain embodiments, the sarcoma can be selected from the group consisting of: osteosarcoma, chondrosarcoma, leiomyosarcoma, rhabdomyosarcoma, mesothelial sarcoma (mesothelioma), fibrosarcoma, angiosarcoma, liposarcoma, glioma, and astrocytoma. In still another embodiment, the one or more rare variants and/or mutations can be analyzed to detect a presence or absence of, determine the stage of, monitor progression of, and/or classify leukemia. In certain embodiments, the leukemia can be selected from the group consisting of: myelogenous, granulocytic, lymphatic, lymphocytic, and lymphoblastic leukemia. In still another embodiment, the one or more rare variants and/or mutations can be used to detect a presence or absence of, determine the stage of, monitor progression of, and/or classify a lymphoma. In certain embodiments, the lymphoma can be selected from the group consisting of: Hodgkin's lymphoma and Non-Hodgkin's lymphoma.

Sequencing and Bioinformatics

As reviewed above, aspects of the invention include sequencing of nucleic acid molecules to generate a plurality of sequence reads, compilation of a plurality of sequence reads into a sequencing library, and bioinformatic manipulation of the sequence reads and/or sequencing library to determine sequence information from a test sample (e.g., a biological sample). In some embodiments, one or more aspects of the subject methods are conducted using a suitably-programmed computer system, as described further herein.

In certain embodiments, a sample is collected from a subject, followed by enrichment for genetic regions or genetic fragments of interest. For example, in some embodiments, a sample can be enriched by hybridization to a nucleotide array comprising cancer-related genes or gene fragments of interest. In some embodiments, a sample can be enriched for genes of interest (e.g., cancer-associated genes) using other methods known in the art, such as hybrid capture. See, e.g., Lapidus (U.S. Pat. No. 7,666,593), the contents of which is incorporated by reference herein in its entirety. In one hybrid capture method, a solution-based hybridization method is used that includes the use of biotinylated oligonucleotides and streptavidin coated magnetic beads. See, e.g., Duncavage et al., J Mol Diagn. 13(3): 325-333 (2011); and Newman et al., Nat Med. 20(5): 548-554 (2014). Isolation of nucleic acid from a sample in accordance with the methods of the invention can be done according to any method known in the art.

Sequencing may be by any method or combination of methods known in the art. For example, known DNA sequencing techniques include, but are not limited to, classic dideoxy sequencing reactions (Sanger method) using labeled terminators or primers and gel separation in slab or capillary, sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, Polony sequencing, and SOLiD sequencing. Sequencing of separated molecules has more recently been demonstrated by sequential or single extension reactions using polymerases or ligases as well as by single or sequential differential hybridizations with libraries of probes.

One conventional method to perform sequencing is by chain termination and gel separation, as described by Sanger et al., Proc Natl. Acad. Sci. USA, 74(12): 5463 67 (1977), the contents of which are incorporated by reference herein in their entirety. Another conventional sequencing method involves chemical degradation of nucleic acid fragments. See, Maxam et al., Proc. Natl. Acad. Sci., 74: 560 564 (1977), the contents of which are incorporated by reference herein in their entirety. Methods have also been developed based upon sequencing by hybridization. See, e.g., Harris et al., (U.S. patent application number 2009/0156412), the contents of which are incorporated by reference herein in their entirety.

A sequencing technique that can be used in the methods of the provided invention includes, for example, Helicos True Single Molecule Sequencing (tSMS) (Harris T. D. et al. (2008) Science 320:106-109), the contents of which are incorporated by reference herein in their entirety. Further description of tSMS is shown, for example, in Lapidus et al. (U.S. Pat. No. 7,169,560), the contents of which are incorporated by reference herein in their entirety, Lapidus et al. (U.S. patent application publication number 2009/0191565, the contents of which are incorporated by reference herein in their entirety), Quake et al. (U.S. Pat. No. 6,818,395, the contents of which are incorporated by reference herein in their entirety), Harris (U.S. Pat. No. 7,282,337, the contents of which are incorporated by reference herein in their entirety), Quake et al. (U.S. patent application publication number 2002/0164629, the contents of which are incorporated by reference herein in their entirety), and Braslavsky, et al., PNAS (USA), 100: 3960-3964 (2003), the contents of which are incorporated by reference herein in their entirety.

Another example of a DNA sequencing technique that can be used in the methods of the provided invention is 454 sequencing (Roche) (Margulies, M et al. 2005, Nature, 437, 376-380, the contents of which are incorporated by reference herein in their entirety). Another example of a DNA sequencing technique that can be used in the methods of the provided invention is SOLiD technology (Applied Biosystems). Another example of a DNA sequencing technique that can be used in the methods of the provided invention is Ion Torrent sequencing (U.S. patent application publication numbers 2009/0026082, 2009/0127589, 2010/0035252, 2010/0137143, 2010/0188073, 2010/0197507, 2010/0282617, 2010/0300559, 2010/0300895, 2010/0301398, and 2010/0304982, the contents of each of which are incorporated by reference herein in their entirety).

In some embodiments, the sequencing technology is Illumina sequencing. Illumina sequencing is based on the amplification of DNA on a solid surface using fold-back PCR and anchored primers. Genomic DNA can be fragmented, or in the case of cfDNA, fragmentation is not needed due to the already short fragments. Adapters are ligated to the 5'- and 3'-ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated.

Another example of a sequencing technology that can be used in the methods of the provided invention includes the single molecule, real-time (SMRT) technology of Pacific Biosciences. Yet another example of a sequencing technique that can be used in the methods of the provided invention is nanopore sequencing (Soni G V and Meller A. (2007) Clin Chem 53: 1996-2001, the contents of which are incorporated by reference herein in their entirety). Another example of a sequencing technique that can be used in the methods of the provided invention involves using a chemical-sensitive field effect transistor (chemFET) array to sequence DNA (for example, as described in US Patent Application Publication No. 20090026082, the contents of which are incorporated by reference herein in their entirety). Another example of a sequencing technique that can be used in the methods of the provided invention involves using an electron microscope (Moudrianakis E. N. and Beer M. Proc Natl Acad Sci USA. 1965 March; 53:564-71, the contents of which are incorporated by reference herein in their entirety).

If the nucleic acid from the sample is degraded or only a minimal amount of nucleic acid can be obtained from the sample, PCR can be performed on the nucleic acid in order to obtain a sufficient amount of nucleic acid for sequencing (See, e.g., Mullis et al. U.S. Pat. No. 4,683,195, the contents of which are incorporated by reference herein in its entirety).
Biological Samples Aspects of the invention involve obtaining a test sample, e.g., a biological sample, such as a tissue and/or body fluid sample, from a subject for purposes of analyzing a plurality of nucleic acids (e.g., a plurality of RNA molecules) therein. Samples in accordance with embodiments of the invention can be collected in any clinically-acceptable manner. Any test sample suspected of containing a plurality of nucleic acids can be used in conjunction with the methods of the present invention. In some embodiments, a test sample can comprise a tissue, a body fluid, or a combination thereof. In some embodiments, a biological sample is collected from a healthy subject. In some embodiments, a biological sample is collected from a subject who is known to have a particular disease or disorder (e.g., a particular cancer or tumor). In some embodiments, a biological sample is collected from a subject who is suspected of having a particular disease or disorder.

As used herein, the term "tissue" refers to a mass of connected cells and/or extracellular matrix material(s). Non-limiting examples of tissues that are commonly used in conjunction with the present methods include skin, hair, finger nails, endometrial tissue, nasal passage tissue, central nervous system (CNS) tissue, neural tissue, eye tissue, liver tissue, kidney tissue, placental tissue, mammary gland tissue, gastrointestinal tissue, musculoskeletal tissue, genitourinary tissue, bone marrow, and the like, derived from, for example, a human or non-human mammal. Tissue samples in accordance with embodiments of the invention can be prepared and provided in the form of any tissue sample types known in the art, such as, for example and without limitation, formalin-fixed paraffin-embedded (FFPE), fresh, and fresh frozen (FF) tissue samples.

As used herein, the term "body fluid" refers to a liquid material derived from a subject, e.g., a human or non-human mammal. Non-limiting examples of body fluids that are commonly used in conjunction with the present methods include mucous, blood, plasma, serum, serum derivatives, synovial fluid, lymphatic fluid, bile, phlegm, saliva, sweat, tears, sputum, amniotic fluid, menstrual fluid, vaginal fluid, semen, urine, cerebrospinal fluid (CSF), such as lumbar or ventricular CSF, gastric fluid, a liquid sample comprising one or more material(s) derived from a nasal, throat, or buccal swab, a liquid sample comprising one or more materials derived from a lavage procedure, such as a peritoneal, gastric, thoracic, or ductal lavage procedure, and the like.

In some embodiments, a test sample can comprise a fine needle aspirate or biopsied tissue. In some embodiments, a test sample can comprise media containing cells or biological material. In some embodiments, a test sample can comprise a blood clot, for example, a blood clot that has been obtained from whole blood after the serum has been removed. In some embodiments, a test sample can comprise stool. In one preferred embodiment, a test sample is drawn whole blood. In one aspect, only a portion of a whole blood sample is used, such as plasma, red blood cells, white blood cells, and platelets. In some embodiments, a test sample is separated into two or more component parts in conjunction with the present methods. For example, in some embodiments, a whole blood sample is separated into plasma, red blood cell, white blood cell, and platelet components.

In some embodiments, a test sample includes a plurality of nucleic acids not only from the subject from which the test sample was taken, but also from one or more other organisms, such as viral DNA/RNA that is present within the subject at the time of sampling.

Nucleic acid can be extracted from a test sample according to any suitable methods known in the art, and the extracted nucleic acid can be utilized in conjunction with the methods described herein. See, e.g., Maniatis, et al., Molecular Cloning: A Laboratory Manual, Cold Spring Harbor, N.Y., pp. 280-281, 1982, the contents of which are incorporated by reference herein in their entirety.

In one preferred embodiment, cell free nucleic acid (e.g., cell-free DNA (cfDNA) and/or cell-free RNA (cfRNA)) are extracted from a test sample. cfDNA are short base nuclear-derived DNA fragments present in several bodily fluids (e.g. plasma, stool, urine). See, e.g., Mouliere and Rosenfeld, PNAS 112(11): 3178-3179 (March 2015); Jiang et al., PNAS (March 2015); and Mouliere et al., Mol Oncol, 8(5):927-41 (2014). Tumor-derived circulating tumor nucleic acids (e.g., ctDNA and/or ctRNA) constitutes a minority population of cfNAs (i.e., cfDNA and/or cfRNA), in some cases, varying up to about 50%. In some embodiments, ctDNA and/or ctRNA varies depending on tumor stage and tumor type. In some embodiments, ctDNA and/or ctRNA varies from about 0.001% up to about 30%, such as about 0.01% up to about 20%, such as about 0.01% up to about 10%. The covariates of ctDNA and/or ctRNA are not fully understood, but appear to be positively correlated with tumor type, tumor size, and tumor stage. E.g., Bettegowda et al, Sci Trans Med, 2014; Newmann et al, Nat Med, 2014. Despite the challenges associated with the low population of ctDNA/ctRNA in cfNAs, tumor variants have been identified in ctDNA and/or ctRNA across a wide span of cancers. E.g., Bettegowda et al, Sci Trans Med, 2014. Furthermore, analysis of cfDNA and/or cfRNA versus tumor biopsy is less invasive, and methods for analyzing, such as sequencing, enable the identification of sub-clonal heterogeneity. Analysis of cfDNA and/or cfRNA has also been shown to provide for more uniform genome-wide sequencing coverage as compared to tumor tissue biopsies. In some embodiments, a plurality of cfDNA and/or cfRNA are extracted from a sample in a manner that reduces or eliminates co-mingling of cfDNA and genomic DNA. For example, in some embodiments, a sample is processed to isolate a plurality of the cfDNA and/or cfRNA therein in less than about 2 hours, such as less than about 1.5, 1 or 0.5 hours.

A non-limiting example of a procedure for preparing nucleic acid from a blood sample follows. Blood may be collected in 10 mL EDTA tubes (for example, the BD VACUTAINER® family of products from Becton Dickinson, Franklin Lakes, N.J.), or in collection tubes that are adapted for isolation of cfDNA (for example, the CELL FREE DNA BCT® family of products from Streck, Inc., Omaha, Nebr.) can be used to minimize contamination through chemical fixation of nucleated cells, but little contamination from genomic DNA is observed when samples are processed within 2 hours or less, as is the case in some embodiments of the present methods. Beginning with a blood sample, plasma may be extracted by centrifugation, e.g., at 3000 rpm for 10 minutes at room temperature minus brake. Plasma may then be transferred to 1.5 ml tubes in 1 ml aliquots and centrifuged again at 7000 rpm for 10 minutes at room temperature. Supernatants can then be transferred to new 1.5 ml tubes. At this stage, samples can be stored at −80° C. In certain embodiments, samples can be stored at the plasma stage for later processing, as plasma may be more stable than storing extracted cfDNA and/or cfRNA.

Plasma DNA and/or RNA can be extracted using any suitable technique. For example, in some embodiments, plasma DNA and/or RNA can be extracted using one or more commercially available assays, for example, the QIAmp Circulating Nucleic Acid Kit family of products (Qiagen N. V., Venlo Netherlands). In certain embodiments, the following modified elution strategy may be used. DNA and/or RNA may be extracted using, e.g., a QIAmp Circulating Nucleic Acid Kit, following the manufacturer's instructions (maximum amount of plasma allowed per column is 5 mL). If cfDNA and/or cfRNA are being extracted from plasma where the blood was collected in Streck tubes, the reaction time with proteinase K may be doubled from 30 min to 60 min. Preferably, as large a volume as possible should be used (i.e., 5 mL). In various embodiments, a two-step elution may be used to maximize cfDNA and/or cfRNA yield. First, DNA and/or RNA can be eluted using 30 µL of buffer AVE for each column. A minimal amount of buffer necessary to completely cover the membrane can be used in the elution in order to increase cfDNA and/or cfRNA concentration. By decreasing dilution with a small amount of buffer, downstream desiccation of samples can be avoided to prevent melting of double stranded DNA or material loss. Subsequently, about 30 µL of buffer for each column can be eluted. In some embodiments, a second elution may be used to increase DNA and/or RNA yield.

In other embodiments, RNA can be extracted and/or isolated using any suitable technique. For example, in some embodiments, RNA can be extracted using a commercially-available kit and/or protocol, e.g., a QIAamp Circulating Nucleic Acids kit and micro RNA extraction protocol.

In some embodiments, the methods involve DNase treating an extracted nucleic acid sample to remove cell-free DNA from a mixed cfDNA and cfRNA test sample.

Computer Systems and Devices

Aspects of the invention described herein can be performed using any type of computing device, such as a computer, that includes a processor, e.g., a central processing unit, or any combination of computing devices where each device performs at least part of the process or method. In some embodiments, systems and methods described herein may be performed with a handheld device, e.g., a smart tablet, or a smart phone, or a specialty device produced for the system.

Methods of the invention can be performed using software, hardware, firmware, hardwiring, or combinations of any of these. Features implementing functions can also be physically located at various positions, including being distributed such that portions of functions are implemented at different physical locations (e.g., imaging apparatus in one room and host workstation in another, or in separate buildings, for example, with wireless or wired connections).

Processors suitable for the execution of computer programs include, by way of example, both general and special purpose microprocessors, and any one or more processors of any kind of digital computer. Generally, a processor will receive instructions and data from a read-only memory or a random access memory, or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including, by way of example, semiconductor memory devices, (e.g., EPROM, EEPROM, solid state drive (SSD), and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having an I/O device, e.g., a CRT, LCD, LED, or projection device for displaying information to the user and an input or output device such as a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The subject matter described herein can be implemented in a computing system that includes a back-end component (e.g., a data server), a middleware component (e.g., an application server), or a front-end component (e.g., a client computer having a graphical user interface or a web browser through which a user can interact with an implementation of the subject matter described herein), or any combination of such back-end, middleware, and front-end components. The components of the system can be interconnected through a network by any form or medium of digital data communication, e.g., a communication network. For example, a reference set of data may be stored at a remote location and a computer can communicate across a network to access the reference data set for comparison purposes. In other embodiments, however, a reference data set can be stored locally within the computer, and the computer accesses the reference data set within the CPU for comparison purposes. Examples of communication networks include, but are not limited to, cell networks (e.g., 3G or 4G), a local area network (LAN), and a wide area network (WAN), e.g., the Internet.

The subject matter described herein can be implemented as one or more computer program products, such as one or more computer programs tangibly embodied in an information carrier (e.g., in a non-transitory computer-readable medium) for execution by, or to control the operation of, a data processing apparatus (e.g., a programmable processor, a computer, or multiple computers). A computer program (also known as a program, software, software application, app, macro, or code) can be written in any form of programming language, including compiled or interpreted languages (e.g., C, C++, Perl), and it can be deployed in any form, including as a stand-alone program or as a module, component, subroutine, or other unit suitable for use in a computing environment. Systems and methods of the invention can include instructions written in any suitable programming language known in the art, including, without limitation, C, C++, Perl, Java, ActiveX, HTML5, Visual Basic, or JavaScript.

A computer program does not necessarily correspond to a file. A program can be stored in a file or a portion of a file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

A file can be a digital file, for example, stored on a hard drive, SSD, CD, or other tangible, non-transitory medium. A file can be sent from one device to another over a network (e.g., as packets being sent from a server to a client, for example, through a Network Interface Card, modem, wireless card, or similar).

Writing a file according to the invention involves transforming a tangible, non-transitory computer-readable medium, for example, by adding, removing, or rearranging particles (e.g., with a net charge or dipole moment into patterns of magnetization by read/write heads), the patterns then representing new collocations of information about objective physical phenomena desired by, and useful to, the user. In some embodiments, writing involves a physical transformation of material in tangible, non-transitory computer readable media (e.g., with certain optical properties so that optical read/write devices can then read the new and useful collocation of information, e.g., burning a CD-ROM). In some embodiments, writing a file includes transforming a physical flash memory apparatus such as NAND flash memory device and storing information by transforming physical elements in an array of memory cells made from floating-gate transistors. Methods of writing a file are well-known in the art and, for example, can be invoked manually or automatically by a program or by a save command from software or a write command from a programming language.

Suitable computing devices typically include mass memory, at least one graphical user interface, at least one display device, and typically include communication between devices. The mass memory illustrates a type of computer-readable media, namely computer storage media. Computer storage media may include volatile, nonvolatile, removable, and non-removable media implemented in any method or technology for storage of information, such as computer readable instructions, data structures, program modules, or other data. Examples of computer storage media include RAM, ROM, EEPROM, flash memory, or other memory technology, CD-ROM, digital versatile disks (DVD) or other optical storage, magnetic cassettes, magnetic tape, magnetic disk storage or other magnetic storage devices, Radiofrequency Identification (RFID) tags or chips, or any other medium that can be used to store the desired information, and which can be accessed by a computing device.

Functions described herein can be implemented using software, hardware, firmware, hardwiring, or combinations of any of these. Any of the software can be physically located at various positions, including being distributed such that portions of the functions are implemented at different physical locations.

As one skilled in the art would recognize as necessary or best-suited for performance of the methods of the invention, a computer system for implementing some or all of the described inventive methods can include one or more processors (e.g., a central processing unit (CPU) a graphics processing unit (GPU), or both), main memory and static memory, which communicate with each other via a bus.

A processor will generally include a chip, such as a single core or multi-core chip, to provide a central processing unit (CPU). A process may be provided by a chip from Intel or AMD.

Memory can include one or more machine-readable devices on which is stored one or more sets of instructions (e.g., software) which, when executed by the processor(s) of any one of the disclosed computers can accomplish some or all of the methodologies or functions described herein. The software may also reside, completely or at least partially, within the main memory and/or within the processor during execution thereof by the computer system. Preferably, each computer includes a non-transitory memory such as a solid state drive, flash drive, disk drive, hard drive, etc.

While the machine-readable devices can in an exemplary embodiment be a single medium, the term "machine-readable device" should be taken to include a single medium or multiple media (e.g., a centralized or distributed database, and/or associated caches and servers) that store the one or more sets of instructions and/or data. These terms shall also be taken to include any medium or media that are capable of storing, encoding, or holding a set of instructions for execution by the machine and that cause the machine to perform any one or more of the methodologies of the present invention. These terms shall accordingly be taken to include, but not be limited to, one or more solid-state memories (e.g., subscriber identity module (SIM) card, secure digital card (SD card), micro SD card, or solid-state drive (SSD)), optical and magnetic media, and/or any other tangible storage medium or media.

A computer of the invention will generally include one or more I/O device such as, for example, one or more of a video display unit (e.g., a liquid crystal display (LCD) or a cathode ray tube (CRT)), an alphanumeric input device (e.g., a keyboard), a cursor control device (e.g., a mouse), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem.

Any of the software can be physically located at various positions, including being distributed such that portions of the functions are implemented at different physical locations.

Additionally, systems of the invention can be provided to include reference data. Any suitable genomic data may be stored for use within the system. Examples include, but are not limited to: comprehensive, multi-dimensional maps of the key genomic changes in major types and subtypes of cancer from The Cancer Genome Atlas (TCGA); a catalog of genomic abnormalities from The International Cancer Genome Consortium (ICGC); a catalog of somatic mutations in cancer from COSMIC; the latest builds of the human genome and other popular model organisms; up-to-date reference SNPs from dbSNP; gold standard indels from the 1000 Genomes Project and the Broad Institute; exome capture kit annotations from Illumina, Agilent, Nimblegen, and Ion Torrent; transcript annotations; small test data for experimenting with pipelines (e.g., for new users).

In some embodiments, data is made available within the context of a database included in a system. Any suitable database structure may be used including relational databases, object-oriented databases, and others. In some embodiments, reference data is stored in a relational database such as a "not-only SQL" (NoSQL) database. In certain embodiments, a graph database is included within systems of the invention. It is also to be understood that the term "database" as used herein is not limited to one single database; rather, multiple databases can be included in a system. For example, a database can include two, three, four, five, six, seven, eight, nine, ten, fifteen, twenty, or more individual databases, including any integer of databases therein, in accordance with embodiments of the invention. For example, one database can contain public reference data, a second database can contain test data from a patient, a third database can contain data from healthy individuals, and a fourth database can contain data from sick individuals with a known condition or disorder. It is to be understood that any other configuration of databases with respect to the data contained therein is also contemplated by the methods described herein.

References and citations to other documents, such as patents, patent applications, patent publications, journals, books, papers, web contents, have been made throughout this disclosure. All such documents are hereby incorporated herein by reference in their entirety for all purposes.

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof. All references cited throughout the specification are expressly incorporated by reference herein.

The foregoing detailed description of embodiments refers to the accompanying drawings, which illustrate specific embodiments of the present disclosure. Other embodiments having different structures and operations do not depart from the scope of the present disclosure. The term "the invention" or the like is used with reference to certain specific examples of the many alternative aspects or embodiments of the applicants' invention set forth in this specification, and neither its use nor its absence is intended to limit the scope of the applicants' invention or the scope of the claims. This specification is divided into sections for the convenience of the reader only. Headings should not be construed as limiting of the scope of the invention. The definitions are intended as a part of the description of the invention. It will be understood that various details of the present invention may be changed without departing from the scope of the present invention. Furthermore, the foregoing description is for the purpose of illustration only, and not for the purpose of limitation.

While the present invention has been described with reference to the specific embodiments thereof, it should be understood by those skilled in the art that various changes may be made and equivalents may be substituted without departing from the true spirit and scope of the invention. In addition, many modifications may be made to adapt to a particular situation, material, composition of matter, process, process step or steps, to the objective, spirit and scope of the present invention. All such modifications are intended to be within the scope of the claims appended hereto.

What is claimed is:

1. A method for correcting sequencing derived errors in sequence reads, the method comprising:
   (a) obtaining a test sample comprising a plurality of cell-free DNA (cfDNA) molecules comprising a plurality of double-stranded DNA (dsDNA) fragments;
   (b) preparing a sequencing library, wherein preparing the sequencing library comprises:
      (i) providing a set of loop-shaped DNA adapters, wherein the set of loop-shaped DNA adapters comprises:
         a plurality of first loop-shaped DNA adapters where each of the first loop-shaped DNA adapters comprises a single DNA molecule comprising:
            (A) two complementary regions that hybridize with one another and leave an unpaired loop at the end of the DNA molecule;
            (B) an endonuclease restriction site in the unpaired loop; and
            (C) a single first unique molecular identifier (UMI);
         a plurality of second loop-shaped DNA adapters where each of the second loop-shaped DNA adapters comprises a single DNA molecule comprising:
            (A) two complementary regions that hybridize with one another and leave an unpaired loop at the end of the DNA molecule; and
            (B) a single second unique molecular identifier (UMI);
      (ii) ligating the plurality of first loop-shaped DNA adapters to a first end of the dsDNA fragments and ligating the plurality second loop-shaped DNA adapters to a second end of the dsDNA fragments to generate a plurality of circular-shaped constructs, wherein each circular-shaped construct comprises a first loop-shaped DNA adapter ligated to a first end of the dsDNA fragment and a second loop-shaped DNA adapter ligated to a second end of the dsDNA fragment; and
      (iii) after step (ii), cleaving the plurality of first loop-shaped DNA adapters with an endonuclease to produce a plurality of linear single-stranded DNA (ssDNA) molecules, wherein said linear ssDNA molecules comprise a forward strand and a reverse complement strand;

(c) sequencing a plurality of the linear ssDNA molecules in the sequencing library to generate a plurality of sequence reads;

(d) grouping the plurality of sequence reads into a plurality of families based on the first UMI and the second UMI, such that one or more unique nucleic acid sequence fragments originating from the same test sample contains the first UMI and the second UMI;
  (i) including in the plurality of families each of the sequence reads that comprises both the first UMI and the second UMI, and
  (ii) excluding from the plurality of families sequence reads that only comprise the first UMI on both ends of a dsDNA fragment or the second UMI on both ends of the dsDNA fragment;

(e) comparing the forward strand and the reverse complement strand of each of the sequence reads within each family of the plurality of families to generate a consensus sequence for each family, wherein the consensus sequence comprises a sequence of nucleotide bases, and wherein each nucleotide base is identified at a given position in the consensus sequence when a specific nucleotide base is present at the position in at least 70% of the sequence reads of family members within each family of the plurality of families;

(f) aligning the consensus sequence for each family of the plurality of families to a reference sequence; and (g) identifying a consensus sequence as comprising a sequencing-derived error in the sequence reads if the consensus sequence differs from the reference sequence at one or more nucleotide base positions.

2. The method according to claim 1, wherein the consensus sequence for each family comprises a sequence of nucleotide bases, wherein each nucleotide base is identified at a given position in the consensus sequence when a specific nucleotide base is present in at least 80% of the sequence reads of family members within each family of the plurality of families.

3. The method according to claim 1, wherein the consensus sequence comprises a sequence of nucleotide bases, wherein each nucleotide base is identified at a given position in the consensus sequence when a specific nucleotide base is present in at least 90% of the sequence reads of family members within each family of the plurality of families.

4. The method according to claim 1, wherein the consensus sequence comprises a sequence of nucleotide bases, wherein each nucleotide base is identified at a given position in the consensus sequence when a specific nucleotide base is present in at least 95% of the sequence reads of family members within each family of the plurality of families.

5. The method according to claim 1, wherein the step of sequencing a plurality of the linear ssDNA molecules in the sequencing library comprises sequencing by a next-generation sequencing (NGS) procedure.

6. The method according to claim 1, wherein the step of sequencing a plurality of the linear ssDNA molecules in the sequencing library comprises a sequencing-by-synthesis procedure.

7. The method according to claim 1, wherein the step of sequencing a plurality of the linear ssDNA molecules in the sequencing library comprises a paired-end sequencing procedure.

8. The method of claim 1, wherein the step of sequencing a plurality of the linear ssDNA molecules in the sequencing library comprises a single molecule sequencing procedure.

9. The method of claim 5, wherein the NGS procedure comprises single-molecule real-time sequencing.

* * * * *